(12) United States Patent
Li

(10) Patent No.: US 7,427,468 B2
(45) Date of Patent: Sep. 23, 2008

(54) ANTI-TSG101 ANTIBODIES AND THEIR USES FOR TREATMENT OF VIRAL INFECTIONS

(75) Inventor: Limin Li, North Bethesda, MD (US)

(73) Assignee: Functional Genetics, Inc., Gaithersburg, MD (US)

( * ) Notice: Subject to any disclaimer, the term of this patent is extended or adjusted under 35 U.S.C. 154(b) by 611 days.

(21) Appl. No.: 10/675,979

(22) Filed: Oct. 1, 2003

(65) Prior Publication Data
US 2004/0223972 A1   Nov. 11, 2004

Related U.S. Application Data

(60) Provisional application No. 60/415,299, filed on Oct. 1, 2002.

(51) Int. Cl.
C12N 1/70 (2006.01)
G01N 33/53 (2006.01)
A61K 39/21 (2006.01)

(52) U.S. Cl. .................. 435/5; 435/7.1; 424/207.1; 424/208.1

(58) Field of Classification Search .............. None
See application file for complete search history.

(56) References Cited

U.S. PATENT DOCUMENTS

2002/0177207 A1   11/2002   Sugiyama et al.
2003/0171318 A1   9/2003    Morham et al.

FOREIGN PATENT DOCUMENTS

WO   WO 02/072790    9/2002
WO   WO 2004/039311  5/2004

OTHER PUBLICATIONS

Leller Ma et al. "Passive immunity in prevention and treatment of infectious diseases". Clin Microbiol Rev. Oct. 2000;13(4):602-14.*
Trkola A te al. "Delay of HIV-1 rebound after cessation of antiretroviral therapy through passive transfer of human neutralizing antibodies" Nature Medicine 11, 615-622 (2005).*
Senior K "Budding new HIV therapies?" Drug Discovery Today, vol. 6, No. 23, pp. 1184-1186 (2001).*
Supplementary Partial European Search Report dated Nov. 17, 2005.
Oh, et al., Negative regulation of cell growth and differentiation by TSG101 through association with p21$^{Cip1/WAF1}$, Proc. Natl. Acad. Sci. USA, vol. 99, No. 8, pp. 5430-5435, 2002.
Krempler, et al., "Targeted Deletion of the *Tsg101* Gene Results in Cell Cycle Arrest at $G_1$/S and p53-independent Cell Death", Jour. Biol. Chem., vol. 277, No. 45, pp. 43216-41223, 2002.
Wagner, et al., "Tsg101 Is Essential for Cell Growth, Proliferation, and Cell Survival of Embryonic and Adult Tissues", Mol. and Cell Biol., vol. 23, No. 1, pp. 150-162, 2003.
Bishop, et al., "Mammalian call E vps proteins recognize ubiquitin and act in the removal of endosomal protein-ubiquitin conjugates", Jour. Cell Biol., vol. 157, No. 1, pp. 91-101, 2002.
Li, et al., "A TSG101/MDM2 regulatory loop modulates MDM2 degradation and MDM2/p53 feedback control", Proc. Natl. Acad. Sci. USA, vol. 98, No. 4, pp. 1619-1624, 2001.
Ruland, et al., "p53 Accumulation, defective cell proliferation, and early embryonic lethality in mice lacking *tsg101*", Proc. Natl. Acad. Sci. USA, vol. 98, No. 4, pp. 1859-1864, 2001.
Moyret-Lalle, et al., "p53 Induction Prevents Accumulation of Aberrant Transcripts in Cancer Cells", Cancer Research, vol. 61, pp. 486-488, 2001.
Göttlinger, et al., "Effect of mutations affecting the p6 *gag* protein on human immunodeficiency virus particle release", Proc. Natl. Acad. Sci. USA, vol. 88, pp. 3195-3199, 1991.
Huang, et al., "p6$^{Gag}$ Is Required for Particle Production from Full-Length Human Immunodeficiency Virus Type 1 Molecular Clones Expressing Protease", Jour. Virol., vol. 69, No. 11, pp. 6810-6818, 1995.
Parent, et al., "Positionally Independent and Exchangeable Late Budding Functions of the Rous Sarcoma Virus and Human Immunodeficiency Virus Gag Proteins", Jour. Virol. vol. 69, No. 9, pp. 5455-5460, 1995.
Yuan, et al., "Mutations altering the Moloney murine leukemia virus p12 Gag protein affect virion production and early events of the virus life cycle", The EMBO Jour., vol. 18, No. 17, pp. 4700-4710, 1999.
Yasuda, et al., "A Proline-Rich Motif (PPPY) in the Gag Polyprotein of Mason-Pfizer Monkey Virus Plays a Maturation-Independent Role in Virion Release", Jour. Virol. vol. 72, No. 5, pp. 4095-4103, 1998.
Puffer, et al., "Equine Infectious Anemia Virus Utilizes a YXXL Motif within the Late Assembly Domain of the Gag p9 Protein", Jour. Virol., vol. 71, No. 9, pp. 6541-6546, 1997.
Wills, et al., "An Assembly Domain of the Rous Sarcoma Virus Gag Protein Required Late in Budding", Jour. Virol., vol. 68, No. 10, pp. 6605-6618, 1994.
VerPlank, et al., "Tsg101, a homologue of ubiquitin-conjugating (E2) enzymes, binds the L domain in HIV type 1 Pr55$^{Gag}$", Proc. Natl. Acad. Sci. USA, vol. 98, No. 14, pp. 7724-7729, 2001.
Garrus, et al., "Tsg101 and the Vacuolar Protein Sorting Pathway Are Essential for HIV-1 Budding", Cell, vol. 107, pp. 55-65, 2001.
Martin-Serrano, et al., "HIV-1 and Ebola virus encode small peptide motifs that recruit Tsg101 to sites of particle assembly to facilitate egress", Nature Medicine, vol. 7, No. 12, pp. 1313-1319, 2001.
Pornillos, et al., "Structure and functional interactions of the Tsg101 UEV domain", The EMBO Jour., vol. 21, No. 10, pp. 2397-2406, 2002.
Demirov, et al., "Overexpression of the N-terminal domain of TSG101 inhibits HIV-1 budding by blocking late domain function", Proc. Natl. Acad. Sci. USA, vol. 99, No. 2, pp. 955-960, 2002.
Patnaik, et al. "Ubiquitin is part of the retrovirus budding machinery", Proc. Natl. Acad. Sci. USA, vol. 97, No. 24, pp. 13069-13074, 2000.

(Continued)

*Primary Examiner*—Zachariah Lucas
*Assistant Examiner*—Bo Peng
(74) *Attorney, Agent, or Firm*—Steven B. Kelber

(57) ABSTRACT

The present invention provides methods of using antibodies that bind a TSG101 protein to inhibit or reduce viral production. The invention also provides methods of using the TSG101 antibodies for the treatment of viral infections, including HIV infection. The invention further provides methods of detecting viral infected cells using TSG101 antibodies.

6 Claims, 15 Drawing Sheets

OTHER PUBLICATIONS

Schubert, et al., "Proteasome inhibition interferes with Gag polyprotein processing, release, and maturation of HIV-1 and HIV-2", Proc. Natl. Acad. Sci. USA, vol. 97, No. 24, pp. 13057-13062, 2000.

Strack, et al., "A role for ubiquitin ligase recruitment in retrovirus release", Proc. Natl. Acad. Sci. USA, vol. 97, No. 24, pp. 13063-13068, 2000.

Bishop, et al., "TSG101/Mammalian VPS23 and Mammalian VPS28 Interact Directly and Are Recruited to VPS4-induced Endosomes", Jour. Cell Biol., vol. 276, No. 15, pp. 11735-11742, 2001.

Little, et al., "Antiretroviral-Drug Resistance Among Patients Recently Infected With HIV", New. Eng. Jour. Med., vol. 347, No. 6, pp. 385-394, 2002.

* cited by examiner

MAVSESQLKKMVSKYKYRDLTVRETVNVITLYKDLKPVLDSYVFNDGSSRELMNLT
GTIPVPYRGNTYNIPICLWLLDTYPYNPPICFVKPTSSMTIKTGKHVDANGKIYLPYLH
EWKHPQSDLLGLIQVMIVVFGDEPPVFSRPISASYPPYQATGPPNTSYMPGMPGGI
SPYPSGYPPNPSGYPGCPYPPGGPYPATTSSQYPSQPPVTTVGPSRDGTISEDTIR
ASLISAVSDKLRWRMKEEMDRAQAELNALKRTEEDLKKGHQKLEEMVTRLDQEVA
EVDKNIELLKKKDEELSSALEKMENQSENNDIDEVIIPTAPLYKQILNLYAEENAIEDTI
FYLGEALRRGVIDLDVFLKHVRLLSRKQFQLRALMQKARKTAGLSDLY

SEQUENCE LISTING

<160> NUMBER OF SEQ ID NOS: 3

<210> SEQ ID NO 1
<211> LENGTH: 390
<212> TYPE: PRT
<213> ORGANISM: Homo sapiens

<400> SEQUENCE: 1

```
Met Ala Val Ser Glu Ser Gln Leu Lys Lys Met Val Ser Lys Tyr Lys
 1               5                  10                  15

Tyr Arg Asp Leu Thr Val Arg Glu Thr Val Asn Val Ile Thr Leu Tyr
                20                  25                  30

Lys Asp Leu Lys Pro Val Leu Asp Ser Tyr Val Phe Asn Asp Gly Ser
            35                  40                  45

Ser Arg Glu Leu Met Asn Leu Thr Gly Thr Ile Pro Val Pro Tyr Arg
        50                  55                  60

Gly Asn Thr Tyr Asn Ile Pro Ile Cys Leu Trp Leu Leu Asp Thr Tyr
65                  70                  75                  80

Pro Tyr Asn Pro Pro Ile Cys Phe Val Lys Pro Thr Ser Ser Met Thr
                85                  90                  95

Ile Lys Thr Gly Lys His Val Asp Ala Asn Gly Lys Ile Tyr Leu Pro
            100                 105                 110

Tyr Leu His Glu Trp Lys His Pro Gln Ser Asp Leu Leu Gly Leu Ile
```

-continued

```
                115                 120                 125
Gln Val Met Ile Val Val Phe Gly Asp Glu Pro Pro Val Phe Ser Arg
    130                 135                 140
Pro Ile Ser Ala Ser Tyr Pro Pro Tyr Gln Ala Thr Gly Pro Pro Asn
145                 150                 155                 160
Thr Ser Tyr Met Pro Gly Met Pro Gly Ile Ser Pro Tyr Pro Ser
            165                 170                 175
Gly Tyr Pro Pro Asn Pro Ser Gly Tyr Pro Gly Cys Pro Tyr Pro Pro
            180                 185                 190
Gly Gly Pro Tyr Pro Ala Thr Thr Ser Ser Gln Tyr Pro Ser Gln Pro
            195                 200                 205
Pro Val Thr Thr Val Gly Pro Ser Arg Asp Gly Thr Ile Ser Glu Asp
    210                 215                 220
Thr Ile Arg Ala Ser Leu Ile Ser Ala Val Ser Asp Lys Leu Arg Trp
225                 230                 235                 240
Arg Met Lys Glu Glu Met Asp Arg Ala Gln Ala Glu Leu Asn Ala Leu
                245                 250                 255
Lys Arg Thr Glu Glu Asp Leu Lys Lys Gly His Gln Lys Leu Glu Glu
                260                 265                 270
Met Val Thr Arg Leu Asp Gln Glu Val Ala Glu Val Asp Lys Asn Ile
            275                 280                 285
Glu Leu Leu Lys Lys Lys Asp Glu Glu Leu Ser Ser Ala Leu Glu Lys
            290                 295                 300
Met Glu Asn Gln Ser Glu Asn Asn Asp Ile Asp Glu Val Ile Ile Pro
305                 310                 315                 320
Thr Ala Pro Leu Tyr Lys Gln Ile Leu Asn Leu Tyr Ala Glu Glu Asn
                325                 330                 335
Ala Ile Glu Asp Thr Ile Phe Tyr Leu Gly Glu Ala Leu Arg Arg Gly
            340                 345                 350
Val Ile Asp Leu Asp Val Phe Leu Lys His Val Arg Leu Leu Ser Arg
            355                 360                 365
Lys Gln Phe Gln Leu Arg Ala Leu Met Gln Lys Ala Arg Lys Thr Ala
    370                 375                 380
Gly Leu Ser Asp Leu Tyr
385                 390

<210> SEQ ID NO 2
<211> LENGTH: 18
<212> TYPE: PRT
<213> ORGANISM: Homo sapiens

<400> SEQUENCE: 2

Val Arg Glu Thr Val Asn Val Ile Thr Leu Tyr Lys Asp Leu Lys Pro
1               5                   10                  15

Val Leu

<210> SEQ ID NO 3
<211> LENGTH: 19
<212> TYPE: PRT
<213> ORGANISM: Homo sapiens

<400> SEQUENCE: 3

Gln Leu Arg Ala Leu Met Gln Lys Ala Arg Lys Thr Ala Gly Leu Ser
1               5                   10                  15

Asp Leu Tyr
```

ANTI-TSG101 ANTIBODIES AND THEIR USES FOR TREATMENT OF VIRAL INFECTIONS

This application claims the benefit under 35 U.S.C. § 119(e) of U.S. Provisional Patent Application No. 60/415,299, filed on Oct. 1, 2002, which is incorporated by reference herein in its entirety.

1. FIELD OF THE INVENTION

The present invention relates to antibodies that bind a TSG101 protein and inhibit or reduce viral production. The invention also relates to methods of using the TSG1O1 antibodies for the treatment of viral infections, including HIV infection. The invention further relates to methods of detecting viral infected cells using TSG101 antibodies.

2. BACKGROUND OF THE INVENTION

Pathogen and host cell interactions play critical roles in the pathogenesis of viral diseases such as AIDS. For a typical viral infection, viruses have to attach to the host cells through cell surface receptors, fuse with host cell membrane, translocate across the cell membrane, uncoat viral particles, synthesize and assemble viral proteins using host protein synthesis machinery, and release from host cells through host exporting machinery. The interplay between the viruses and host cells determine the outcome of viral pathogenesis, ranging from the elimination of viruses to a parasitic or lethal infection. For example, HIV employs a variety of strategies to productively infect human cells. A retrovirus, its life cycle begins by attaching to host cells—the primary target is the CD4+ T helper cells and gaining entry via specific receptors. In the cell, the RNA genome is "reverse" transcribed to its complementary DNA, and then shuttled to the nucleus for its integration in the host genome. This integrated "provirus" then directs the production of new viral RNA and proteins, which self-assemble and then "bud" from the cell as mature- and infectious-viral particles, enveloped in plasma membrane. Like all viruses, the HIV is a parasite, unable to catalyze the membrane fission event that drives the budding process. Instead, the nascent virus recruits the cell's membrane sorting machinery to complete this final stage of infection. Such an host and virus interplay has been well demonstrated in individuals, who carry a defective cell surface receptor (CCR5), are completely resistant to HIV infection, elucidating the important roles of host genes and genetic pathways in viral pathogenesis.

Tumor Susceptibility Gene 101 (TSG101, Li et al., 1996, Cell 85, 319-29) plays important roles in cell growth (Zhong et al., 1998, Cancer Res 58, 2699-702; Oh et al., 2002, Proc Natl Acad Sci USA 99, 5430-5; Krempler et al., 2002, J Biol Chem 277, 43216-23; Wagner et al., 2003, Mol Cell Biol 23, 150-62; Li et al., 1996, Cell 85, 319-29), cellular protein trafficking (Babst et al., 2000, Traffic 1, 248-58; Bishop et al., 2002, J Cell Biol 157, 91-101), and degradation of p53 (Li et al., 2001, Proc Natl Acad Sci USA 98, 1619-24; Ruland et al., 2001, Proc Natl Acad Sci USA 98, 1859-64; Moyret-Lalle et al., 2001, Cancer Res 61, 486-8). TSG101 is also widely recognized as a key player in this final stage, inhibition of cellular TSG101 blocks the budding process of HIV. Acting in concert with other cellular factors, TSG 101 thus plays an essential role in the budding or spread of HIV viruses. The HIV Gag protein, previously shown to orchestrate viral assembly and budding, binds with high affinity to TSG 101, and this Gag/TSG101 interaction is essential for efficient HIV viral assembling and budding, as disruption of the Gag/TSG101 interaction prevents HIV viral budding, and significantly limit the spread of HIV virus.

The final step in the assembly of an enveloped virus assembly requires separation of budding particles from the cellular membranes. Three distinct functional domains in Gag, i.e., PTAP in HIV-1 (Gottlinger et al., 1991, Proc Natl Acad Sci USA 88, 3195-9; Huang et al., 1995, J Virol 69, 6810-8); PPPY in RSV (Parent et al. 1995, J Virol 69, 5455-60), MuLV (Yuan et al., 1999, Embo J 18, 4700-10), and M-PMV (Yasuda et al., 1998, J Virol 72, 4095-103); and YXXL in EIAV (Puffer et al., 1997, J Virol 71, 6541-6), have been identified in different retroviruses that are required for this function and have been termed late, or L domains (Wills et al., 1991, Aids 5, 639-54). In HIV-1, the L domain contains a PTAP motif and is required for efficient HIV-1 release (see, e.g., Wills et al., 1994, J. Virol. 68, 6605-6618; Göttlinger et al., 1991, Proc. Natl. Acad Sci. USA 88, 3195-3199; Huang et al., 1995, J. Virol. 69, 6810-6818). The L domain of HIV-1 p6, especially the PTAP motif, binds to the cellular protein TSG101 and recruits it to the site of virus assembly to promote virus budding (VerPlank et al., 2001, Proc. Natl. Acad. Sci. USA 98:7724-7729; Garrus et al., 2001, Cell 107:55-65; Martin-Serrano et. al., 2001, Nature Medicine 7:1313-19; Pornillos et al., 2002, EMBO J. 21:2397-2406; Demirov et al., 2002, Proc. Natl. Acad. Sci. USA 99:955-960; PCT Publication WO 02/072790; U.S. patent application Publication No. US 2002/0177207). The UEV domain of TSG101 binds the PTAP motif and mono-ubiquitin (Pornillos et al., 2002, Embo J 21, 2397-406; Pornillos et al., 2002, Nat Struct Biol 9, 812-7), which has also been implicated in HIV-1 budding (Patnaik et al., 2000, Proc Natl Acad Sci USA 97, 13069-74; Schubert et al., 2000, Proc Natl Acad Sci USA 97, 13057-62; Strack et al., 2000, Proc Natl Acad Sci USA 97, 13063-8). Depletion of cellular TSG101 (Garrus et al., 2001, Cell 107:55-65) or over-expression of a truncated form of TSG101 inhibits HIV-1 release (Demirov et al., 2002, Proc. Natl. Acad. Sci. USA 99:955-960). Under certain circumstances, TSG101 can even substitute for the HIV-1 L domain to promote virus release (Martin-Serrano et. al., 2001, Nature Medicine 7:1313-19).

In yeast, the Tsg101 ortholog Vps23 has been shown to interact with Vps28 and Vps37 and to form a protein complex named ESCRT-I, which is critical for endosomal protein sorting into the multivesicular body pathway (Katzmann et al., 2001, Cell 106, 145-55). It is hypothesized that this intracellular multivesicular body formation resembles HIV-1 release at the plasma membrane (Garrus et al., 2001, Cell 107:55-65; Patnaik et al., 2000, Proc Natl Acad Sci USA 97, 13069-74). In mammalian cells, TSG101 interacts with Vps28 to form an ESCRT-I-like complex (Babst et al., 2000, Traffic 1, 248-58; Bishop et al., 2002, J Cell Biol 157, 91-101; Bishop et al., 2001, J Biol Chem 276, 11735-42), although the mammalian homolog of Vps37 has not been identified.

Recent studies (Blower et al., 2003, AIDS Rev. 5:113-25; Valdiserri et al., 2003, Nat Med. 9:881-6) have estimated that as many as 42 million people worldwide have been infected with HIV. The disease has killed more than 3 million people. While the advent of highly potent and targeted combination therapies has slowed the progression of AIDS in industrialized nations, the AIDS pandemic is causing a "human development catastrophe" in developing nations, particularly in Africa, where more than 21 million Africans have been infected. In South Africa alone, the death toll is projected to rise to 10 million by 2015. Related statistics portend a similar crisis in the Asia Pacific region, which, according to United Nations' estimates, has more than 7 million HIV-infected individuals. Repercussions from the AIDS pandemic extend well beyond the clinic, which lack the resources to treat the swelling numbers of recently infected patients (nearly 20% of the adult population in South Africa is infected). Treatment of HIV-infected and gravely ill AIDS patients is stressing the already over-burdened health care systems of Africa and other developing nations. Worse yet, current treatments for HIV—despite their initial success in reducing viral load—are beginning to lose their efficacy, as drug-resistant HIV strains are increasingly isolated in newly infected individuals. Further compounding the therapeutic management of HIV disease is the toxicity of current antiretroviral regimens, the magnitude of which complicates the physician's decision to begin and to maintain treatment. Identifying new therapeutic paradigms for the treatment of HIV disease, especially those with mechanisms of action that promise to slow the development of resistance, is indeed a global challenge for the biopharmaceutical industry.

Many viruses are also highly mutable. Methods and compositions relying on targeting such viruses directly are normally not sufficient in the treatment of infection by such viruses. For example, HIV-1 is a highly mutable virus that during the course of HIV-1 infection, the antibodies generated in an infected individual do not provide permanent protective effect due in part to the rapid emergence of neutralization escape variants (Thali et al., 1992, J. Acquired Immune Deficiency Syndromes 5:591-599). Current therapies for the treatment of HIV-infected individuals focus primarily on viral enzymes involved in two distinct stages of HIV infection, the replication of the viral genome and the maturation of viral proteins. Since the virus frequently mutates, strains resistant to an antiviral inhibitor develop quickly, despite the drug's initial therapeutic effects. In one recent study, the percentage of individuals newly infected with drug-resistant HIV strains increased six fold over a five year period (Little et al., 2002, N Engl J Med. 347:385-94). Further, combination therapy, the current standard of care that attacks HIV with inhibitors of both reverse transcriptase and protease, is leading to the development of multi-drug resistant HIV strains. Antiretroviral drugs directed against new HIV-based targets, while of considerable value, do not address this increasingly critical issue. For example, HIV strains resistant to Fuzeon® (enfuvirtide), the newest addition to the anti-HIV armamentarium, have already been isolated from patients. Thus, despite its antiviral potency and novel mechanism of action, drug-resistance is likely to undermine the therapeutic potential of viral fusion inhibitors like Fuzeon®. There is therefore a need for developing novel therapeutics and preventative measures to combat viral infections such as HIV infection.

Discussion or citation of a reference herein shall not be construed as an admission that such reference is prior art to the present invention.

3. SUMMARY OF THE INVENTION

The present invention provides methods of using antibodies that bind a TSG101 protein to inhibit or reduce viral production. The present invention also provides methods of using TSG101 antibodies for treating viral infections. The present invention also provides methods and compositions for treating viral infection by targeting TSG101 on the surface of infected cells, e.g., delivering therapeutic and/or diagnostic agents, to such infected cells.

In one aspect, the invention provides a method for reducing viral budding from a mammalian cell infected by an enveloped virus. The method comprises contacting said mammalian cell with a sufficient amount of an antibody that binds a TSG101 protein. In another aspect, the invention provides a method for delivering a therapeutic molecule to a mammalian cell infected by an enveloped virus, comprising contacting said mammalian cell with an antibody conjugate comprising an antibody that binds a TSG101 protein conjugated with said therapeutic molecule. In a preferred embodiment, said antibody binds the N-terminal or C-terminal region of said TSG101 protein. In a preferred embodiment, said mammalian cell is a human cell. In another preferred embodiment, said antibody binds an epitope comprised in the amino acid region selected from the group consisting of VRETVNVITLYKDLKPVL (SEQ ID NO:2) and QLRALMQKARKTAGLSDLY (SEQ ID NO:3). Preferably, said antibody is a monoclonal antibody. In still another preferred embodiment, said enveloped virus is selected from the group consisting of human immunodeficiency virus type I (HIV-I), human immunodeficiency virus type II (HIV-II), Marburg virus, and Ebola virus.

In another aspect, the invention provides a method for treating infection by an enveloped virus in a mammal, comprising administering to said mammal a therapeutically effective amount of an antibody that binds a TSG101 protein. In still another aspect, the invention provides a method for treating infection by an enveloped virus in a mammal, comprising administering to said mammal a therapeutically effective amount of an antibody conjugate comprising an antibody that binds a TSG101 protein conjugated with a therapeutic agent. In a preferred embodiment, said antibody binds the N-terminal or C-terminal region of said TSG101 protein. In a preferred embodiment, said mammal is a human. In another preferred embodiment, said antibody binds an epitope comprised in the amino acid region selected from the group consisting of VRETVNVITLYKDLKPVL (SEQ ID NO:2) and QLRALMQKARKTAGLSDLY (SEQ ID NO:3). Preferably, said antibody is a monoclonal antibody. In still another preferred embodiment, said enveloped virus is selected from the group consisting of human immunodeficiency virus type I (HIV-I), human immunodeficiency virus type II (HIV-II), Marburg virus, and Ebola virus. In one embodiment, the method further comprises administering to said mammal a therapeutically effective amount of one or more other therapeutic agents.

In still another aspect, the invention provides a method for identifying a mammalian cell infected by an enveloped virus, comprising (a) contacting cells of a mammal with an antibody conjugate comprising an antibody that binds a TSG101 protein conjugated with a label; and (b) detecting a cell having said label attached, thereby identifying said cell infected by said enveloped virus. In a preferred embodiment, said antibody binds the N-terminal or C-terminal region of said TSG101 protein. In a preferred embodiment, said mammalian cell is a human cell. In another preferred embodiment, said antibody binds an epitope comprised in the amino acid region selected from the group consisting of VRETVNVITLYKDLKPVL (SEQ ID NO:2) and QLRALMQKARKTAGLSDLY (SEQ ID NO:3). Preferably, said antibody is a monoclonal antibody. In another preferred embodiment, said enveloped virus is selected from the group consisting of human immunodeficiency virus type I (HIV-I), human immunodeficiency virus type II (HIV-II), Marburg virus, and Ebola virus. In one embodiment, said label is a fluorescence label, and said cell having said label attached is detected using a fluorescence activated cell sorter.

The invention also provides a method for ex vivo removal of cells infected by an enveloped virus from a fluid derived from a mammal. The method comprises (a) incubating said fluid with a sufficient amount of a TSG101 antibody that binds a TSG101 protein; and (b) removing cells bound by said TSG101 antibody from said fluid. Said fluid can be blood or serum. In a preferred embodiment, said antibody binds the N-terminal or C-terminal region of said TSG101 protein. In a preferred embodiment, said mammal is a human. In another preferred embodiment, said antibody binds an epitope comprised in the amino acid region selected from the group consisting of VRETVNVITLYKDLKPVL (SEQ ID NO:2) and QLRALMQKARKTAGLSDLY (SEQ ID NO:3). Preferably, said antibody is a monoclonal antibody. In another preferred embodiment, said enveloped virus is selected from the group consisting of human immunodeficiency virus type I (HIV-I), human immunodeficiency virus type II (HIV-II), Marburg virus, and Ebola virus. In one embodiment, said cells bound by said TSG101 antibody are removed using a column comprising an antibody that binds said TSG101 antibody.

The invention also provides a method for treating or preventing infection by an enveloped virus in a mammal, comprising administering to said mammal a therapeutically or prophylactically sufficient amount of a vaccine composition, wherein said vaccine composition comprises a polypeptide comprising a TSG101 protein. In a preferred embodiment, said polypeptide comprises an N-terminal or C-terminal region of said TSG101 protein. In a preferred embodiment, said mammal is a human. In another preferred embodiment, said polypeptide comprises an amino acid region selected from the group consisting of VRETVNVITLYKDLKPVL (SEQ ID NO:2) and QLRALMQKARKTAGLSDLY (SEQ ID NO:3). In still another preferred embodiment, said enveloped virus is selected from the group consisting of human immunodeficiency virus type I (HIV-I), human immunodeficiency virus type II (HIV-II), Marburg virus, and Ebola virus. In one embodiment, the method further comprises administering to said mammal a therapeutically effective amount of one or more other therapeutic agents.

The invention also provides a method for treating or preventing infection by an enveloped virus in a mammal, comprising administering to said mammal a therapeutically or prophylactically sufficient amount of a DNA vaccine composition, wherein said DNA vaccine composition comprises a polynucleotide molecule encoding a polypeptide comprising a fragment of a TSG101 protein. In one embodiment, said polynucleotide molecule encodes a polypeptide comprising an N-terminal or C-terminal region of said TSG101 protein. In a preferred embodiment, said mammal is a human. In still another preferred embodiment, said polynucleotide molecule encodes a polypeptide comprising amino acid sequence selected from the group consisting of VRETVNVITLYKDLKPVL (SEQ ID NO:2) and QLRALMQKARKTAGLSDLY (SEQ ID NO:3), or a fragment of at least 5 amino acids thereof. In still another preferred embodiment, said enveloped virus is selected from the group consisting of human immunodeficiency virus type I (HIV-I), human immunodeficiency virus type II (HIV-II), Marburg virus, and Ebola virus.

4. BRIEF DESCRIPTION OF THE FIGURES

FIG. 1 depicts the 390 amino acid sequence of human TSG101 protein (SEQ ID NO:1). (GenBank Accession No. U82130.1/GI:1772663).

FIG. 2 depicts the effects of anti-TSG101 antibodies on MLV virus production. Left top panel: phoenix helper cells without treatment of antibody (positive control) showed efficient production of retroviruses, and infection of N2A target cells; left middle panel: Rabbit IgG had no effect; left bottom panel: a rabbit antibody against N-terminal TSG101 had an effect of less than 20% inhibition; right top panel: a rabbit antibody against C-terminal TSG101 significantly inhibited the production of retroviruses, and infection of N2A target cells (50- 70% inhibition); right middle panel: a mixture of anti-C terminal and anti-N terminal antibodies gave similar results as the anti-C terminal antibody alone; right bottom panel: N2a cells that were not infected by viruses only showed minimal background staining.

FIGS. 3A-E: GFP-TSG101 localizes to cell surface during viral release. Live confocal images of Phoenix helper cells with active viral release 24 hrs after transfection of GFP-TSG101. 3A. Bright field images of four cells; 3B-E. Live confocal fluorescence images of the same field at different sections; White arrows point to cell surface localization of GFP-TSG101.

FIG. 4: Cell Surface Localization of TSG101 during HIV budding. H9ΔBgl cells (CD4+ human T lymphocytes, carrying HIV viral integration) were actively producing and releasing HIV virions with a defective envelope protein (this non-infectious form of HIV viruses will not infection other cells, thus specifically allowing the study viral release). The parental H9 cells that do not carry HIV were used as a control. Both H9ΔBgl and H9 cells were fixed with 2% paraformoldehyde for 10 min at room temperature (this surface fixation does not permeabilize cells). Anti-TSG101 antibody were incubated with both cell lines for 20 min and detected with a fluorescence labeled secondary antibody. Top panels: fluorescence images; Bottom panels: bright field images.

FIG. 5: FACS Profile of Cell Surface Localization of TSG101 during HIV Budding. Both H9ΔBgl and H9 cells were fixed with 2% paraformoldehyde for 10 min at room temperature (this surface fixation doesn't permeabilize cells). Anti-TSG101 antibodies were incubated with both cell lines for 20 min and detected with a fluorescent labeled secondary antibody. The immuno-stained cells were analyzed via FACS. Top panel: H9ΔBgl cells, with 85% cells stained positive for surface TSG101; Bottom panel:H9 control cells, with less than 0.1% cells stained positive for surface TSG101.

FIG. 6: Inhibition of HIV-1 production by anti-TSG101 antibodies. Lane 1 and 5, mock transfection; Lane 2 and 6, pNL4-3 and control antibody (rabbit IgG); Lane 3 and 7, pNL4-3 and anti-TSG101 antibody "B"; Lane 4 and 8, pNL4-3 and anti-TSG101 antibody "E".

FIG. 7: Antibody Inhibition of HIV Release from H9ΔBgl cells. HIV producing H9ΔBgl cells were incubated with anti-TSG101 antibody "E" at different concentrations, 48 hours later, viral supernatants were collected and assayed by HIV p24 ELISA kit. Averages of three independent experiments (each with triplicates) were shown. Significant antibody inhibition (* $P<0.05$) of viral release was observed at 80 ug/ml.

FIG. 8: Antibody Inhibition of HIV Infectivity. HIV producing Jurkat cells (infected with Wild-type HIV-1) were incubated with anti-TSG101 antibody "E" at 40 ug/ml, 48 hours later, viral supernatants were collected and used for infection of MAGI cells. assayed by HIV p24 ELISA kit. Averages of three independent experiments (each with triplicates) were shown. Significant antibody inhibition of viral release was observed at 40 ug/ml.

FIGS. 9A-B: Release of Ebola GP and VP40 into culture supernatants. 9A 293T cells were transfected with the indicated plasmids, supernatants were cleared from floating and particulate material were pelleted through 20% sucrose by ultracentrifugation. The individual proteins were detected in the cell lysates and in the particulate material from supernatant by immunoblotting (IB). 9B Supernatants from cells transfected with Ebola VP40 alone or GP+VP40 were immunoprecipitated with anti-GP mAb and analyzed by immunoblotting. Lower panel shows the expression of VP40 in total cell lysates. IgH: immunoglobulin heavy chain from the antibody used for immunoprecipitation.

FIGS. 10A-B: Electron microscopic analysis of virus like particles generated by EBOV GP and VP40. Particles obtained by ultracentrifugation of the supernatants of 293T cells transfected with Ebola GP+VP40 were negatively stained with uranyl-acetate to reveal the ultrastructure (10A), or stained with anti-Ebo-GP mAb followed by Immunogold rabbit anti mouse Ab (10B), and analyzed by electron microscopy.

FIG. 11: Association of VP40 and TSG101 in 293T cells. Cells were transfected with Myc tagged TSG101 full length (FL) or the indicated truncations along with VP40. After 48 h cells were lysed and subjected to immunoprecipitatiopn with anti Myc.

Figure 14:
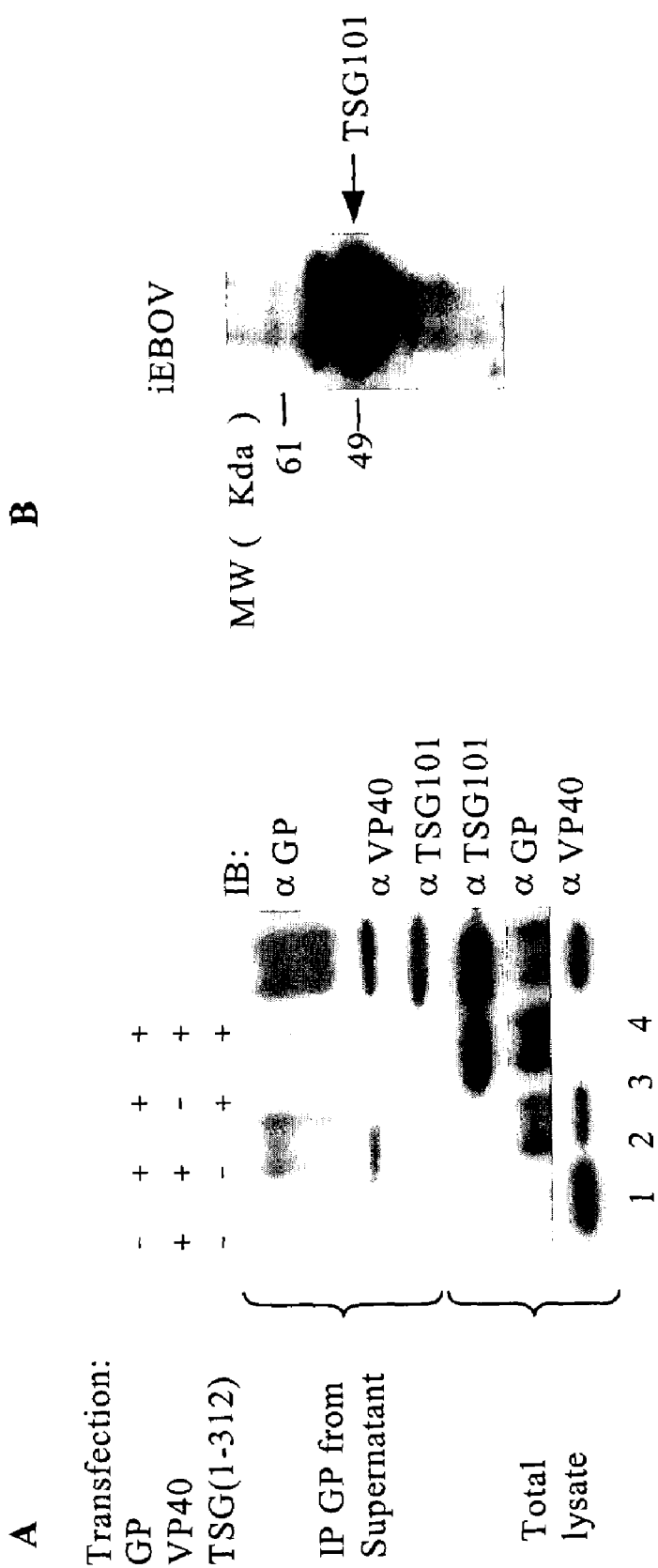

FIGS. 14A-B: Association of TSG101 with Ebola VLPs and inactivated Ebola virus. 14A 293 cells were transfected with the indicated plasmids, supernatants were immunoprecipitated with anti-GP mAb and analyzed by immunoblotting with the antibodies indicated on the right. Lower three panels shows the expression of the transfected proteins in total cell lysates. 14B: 5 µg inactivated Ebola virus (iEBOV) were subjected to SDS-PAGE and Western blot analysis with rabbit anti-TSG101 antibody. The molecular weight markers and position of TSG101 are indicated.

Figure 15:
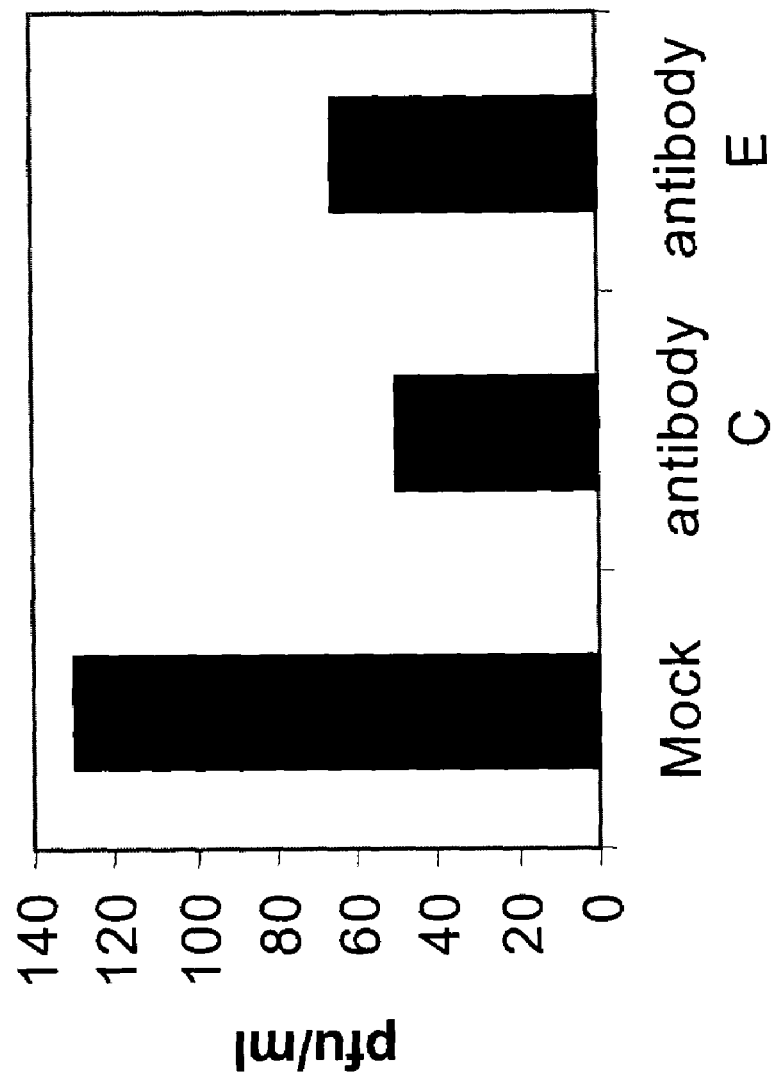

FIG. 15 shows results of inhibition of Ebola virus release in Hela cells by anti TSG101 antibodies.

5. DETAILED DESCRIPTION OF THE INVENTION

The present invention provides methods of using antibodies that bind a TSG101 protein to inhibit or reduce viral production. The present invention also provides methods of using TSG101 antibodies for treating viral infections. The present invention also provides methods and compositions for treating viral infection by targeting TSG101 on the surface of infected cells, e.g., delivering therapeutic and/or diagnostic agents, to such infected cells.

The rational design of therapeutics requires an improved understanding of HIV pathogenesis. Recent studies show that a host protein, TSG101, plays a critical role in the pathogenesis of various viruses such as HIV and Ebola viruses. In particular, TSG101 participates in the process by which viral particles escape, or bud, from infected cells, and therefore represents a novel target for anti-viral drug discovery. Underlying the assembly and release of enveloped RNA viruses from infected cells is a tight coordination between viral and host proteins (Perez et al., 2001, Immunity 15(5): 687-90; Freed, 2002, J Virol 76(10): 4679-87; Pornillos et al., 2002, Trends Cell Biol 12(12): 569-79). While many of the protein: protein and protein: membrane interactions that govern the final stages of infection have yet to be identified, the cellular TSG 101 protein has emerged as a critical player (Garrus et al., 2001, Cell 107:55-65; Carter 2002; Pornillos et al., 2002, Trends Cell Biol 12(12): 569-79; Pornillos et al., 2002, Nat Struct Biol 9, 812-7). Genetic, biochemical and microscopic analyses have shown that TSG101 interacts with multiple enveloped RNA viruses—including members of the retrovirus, rhabdovirus and filovirus families.

Despite their considerable evolutionary divergence, many enveloped RNA viruses employ similar strategies to complete the final stages of infection (Martin-Serrano et. al., 2001, Nature Medicine 7:1313-19; Freed, 2002, J Virol 76(10): 4679-87). Of particular importance to Human Immunodeficiency Virus Type 1 (HIV-1), Vesicular Stomatitis Virus (VSV), Ebola Virus (EBOV), Marburg Virus (MARV) and others is the Late or L domain, a sequence motif that uniquely appropriates cellular pathways to drive viral particle assembly and budding. Three sequence motifs with L-domain activity have been characterized: PPxY, YxxL and PTAP (where "x" denotes any amino acid). HIV-1 budding requires the PTAP motif, found at the amino terminus of the p6Gag protein. Rhabdoviruses, as typified by VSV, utilize the PPxY motif within the Matrix (M) protein. The L-domains of multiple viral families recruit TSG101, a cellular protein critical to endosomal membrane sorting (VerPlank et al., 2001, Proc. Natl. Acad. Sci. USA 98:7724-7729; Pornillos et al., 2002, Nat Struct Biol 9, 812-7). Initially identified by a random knockout screen in mammalian cells, TSG101 is a 43KDa multifunctional protein involved in membrane trafficking, cell cycle control, microtubule assembly and protein degradation (Li et al., 1996, Cell 85, 319-29; Bishop et al., 2001, J Biol Chem 276: 11735-42; Katzmann et al., 2001, Cell 106, 145-55; Li et al., 2001, Proc Natl Acad Sci USA 98, 1619-24. The C-terminus of TSG101 possesses a coiled-coil domain and a domain that auto-regulates its cellular levels; whereas the TSG101 amino-terminus—which interacts with multiple viral L-domains via a binding pocket that structurally and functionally resembles WW and SH3 domains—bears significant homology to Ubiquitin Conjugating (UBC) E2 enzymes (Pornillos et al., 2002, Nat Struct Biol 9, 812-7). Although the UBC-like domain of TSG101 strongly binds ubiquitin, a 76 amino acid protein central to regulating protein turnover and sorting, it lacks the catalytic cysteine residue involved in ubiquitination of target proteins (Hicke, 2001, Cell 106(5): 527-30).

In eukaryotic cells, TSG101 is a component of ESCRT1 (endosomal sorting complex required for transport), a ~350 kDa cytoplasmic complex that also includes Vps28 and Vps37 (Katzmann et al., 2001, Cell 106, 145-55; Bishop et al., 2002, J Cell Biol 157, 91-101). The interaction among these three proteins, and their respective roles in membrane trafficking are currently under investigation. The TSG101 yeast homologue, Vps23, was identified by its functional complementation of protein sorting defects (Babst et al., 2000, Traffic 1, 248-58). Fibroblasts with reduced TSG101 levels and yeast Vps23 null mutants both display defects in the endosomal/MVB pathway. For instance, receptors that would normally enter the MVB system for lysosomal degradation are instead recycled to the surface, leading to profound disturbances in cell signaling. Based on their recent experimental analysis, Katzmann et al have suggested that TSG101/Vps23 binds ubiquitinated proteins at the surface of early endosomes, and facilitates their entry into MVB vesicles (Katzmann et al., 2001, Cell 106, 145-55).

In addition to TSG101, cellular proteins with WW-domains have been shown to interact with the L-domain sequence motifs of enveloped RNA viruses (Harty, et al., 2000, Proc Natl Acad Sci USA 97(25): 13871-6; Kikonyogo et al., 2001, Proc Natl Acad Sci U S A 98(20): 11199-204). For example, Far-Western binding assays have demonstrated a specific interaction with the WW-domains of the mammalian ubiquitin ligase, Nedd4, and its yeast homolog Rsp5, with the VP40 L domain of EBOV (Harty, et al., 2000, Proc Natl Acad Sci USA 97(25): 13871-6; Kikonyogo et al., 2001, Proc Natl Acad Sci USA 98(20): 11199-204). Indeed, the data thus far point to an important role for ubiquitin in viral budding (Patnaik et al., 2000, *Proc Natl Acad Sci USA* 97, 13069-74; Carter, 2002, Trends Microbiol 10(5): 203-5; Myers et al., 2002, J Virol 76(22): 11226-35). There may also be a constitutive interaction between Nedd4 and TSG101. It has been suggested that HIV-1 may exploit Nedd4 and TSG101 to escape from infected cells in a manner wholly unrelated to the endosomal/MVB pathway. Nevertheless, TSG101 is widely regarded as a key host factor appropriated by viruses to drive viral release. The proposed TSG101/MVB link is based, in part, on the biophysical process of MVB formation, which is known to include the invagination of the endosomal lipid bilayer away from the cytoplasm and towards the lumen (Patnaik et al., 2000, *Proc Natl Acad Sci USA* 97, 13069-74; Jasenosky et al., 2001, J Virol 75(11): 5205-14). Enveloped RNA viruses face similar topological parameters: following viral assembly on the inner leaflet of the membrane, the bilayer must evaginate towards the extracellular milieu—again away from the cytoplasm. Devoid of any catalytic ability to split an otherwise thermodynamically stable bilayer, viruses apparently recruit endosomal membrane factors for assistance. The TSG101: L domain interaction may thus provide a vital nexus between nascent virions and the endosomal machinery that drives membrane fission and budding. As discussed above, TSG101, a constituent of ESCRT-1, sorts ubiquitinated proteins for inclusion in the MVB pathway. But this sorting may be subverted in cells infected with HIV and related enveloped RNA viruses. That is, rather than directing ubiquitinated proteins into the MVB pathway, TSG101 and its endosomal counterparts may direct the plasma membrane and its associated viral particles to evaginate, forming enveloped vesicles that pinch off from the plasma membrane.

The molecular determinants that drive virion assembly and release are still an area of active research, though some general conclusions have emerged. First, the recruitment of TSG101 to the plasma membrane during virion maturation is absolutely required. The data supporting a central TSG101 role are compelling: (i) overexpression of the TSG101 UBC domain trans-dominantly disrupts VLP formation in HIV-1 Gag expressing cells (Demirov et al., 2002, Proc. Natl. Acad. Sci. USA 99:955-960); (ii) ablating TSG101 expression via RNA interference impairs HIV-1 budding (Garrus et al., 2001, Cell 107:55-65) and (iii) in both of these instances, electron microscopic analysis demonstrated viral particles tethered to the plasma membrane via membranous stalks, structurally similar to those found in cells expressing L-domain defective viruses. As shown by Martin-Serrano et al., L-domain point mutations that preclude TSG101 binding with the filoviral VP40 or HIV-1 p6Gag, markedly reduce viral particle release from human cells, an effect that coincides with the failure of TSG101 to colocalize with the viral proteins at the lipid bilayer (Martin-Serrano et. al., 2001, Nature Medicine 7:1313-19). Related experiments demonstrated that the EBOV L-domain was able to substitute for the p6Gag L-domain, with no discernible effects on VLP release, underscoring the conserved nature of the enveloped RNA viral budding mechanisms. Significantly, HIV-1 L-domain is dispensable once TSG101 is directed fused to HIV-1 Gag. Therefore the primary responsibility of the L-domain is to recruit TSG101 to the plasma membrane. This interaction between TSG101 and viral L domains represents a novel target for the prevention and treatment of HIV, EBOV and MARV infections (Luban, 2001, Nat Med 7(12): 1278-80; Senior, 2001, Drug Discov Today 6(23): 1184-1186).

The inventor has discovered that anti-TSG101 antibodies can be used for inhibiting or reducing viral infections.

5.1. Anti-TSG101 Antibodies

The invention encompasses the use of an antibody that contains a binding site which specifically binds a TSG101 protein for inhibiting or reducing viral infection. Such anti-TSG101 antibodies can therefore be used as broad spectrum anti-viral agents. The term "antibody" as used herein refers to immunoglobulin molecules. In one embodiment, the antibody binds a C-terminal region of a TSG101 protein. In a preferred embodiment, the antibody binds an epitope comprised in the amino acid region QLRALMQKARKTAGLSDLY (SEQ ID NO:3). In another embodiment, the antibody binds an N-terminal region of a TSG101 protein. In a preferred embodiment, the antibody binds an epitope comprised in the amino acid region VRETVNVITLYKDLKPVL (SEQ ID NO:2).

As used herein, "epitope" refers to an antigenic determinant, i.e., a region of a molecule that provokes an immunological response in a host or is bound by an antibody. This region can but need not comprise consecutive amino acids. The term epitope is also known in the art as "antigenic determinant." An epitope may comprise as few as three amino acids in a spatial conformation which is unique to the immune system of the host. Generally, an epitope consists of at least five such amino acids, and more usually consists of at least 8-10 such amino acids. Methods for determining the spatial conformation of such amino acids are known in the art.

The invention also envisions the use of antibody fragments that contain a binding site which specifically binds a TSG101 protein. Examples of immunologically active fragments of immunoglobulin molecules include F(ab) and F(ab')2 fragments which can be generated by treating the antibody with an enzyme such as pepsin or papain. Examples of methods of generating and expressing immunologically active fragments of antibodies can be found in U.S. Pat. No. 5,648,237 which is incorporated herein by reference in its entirety.

The immunoglobulin molecules are encoded by genes which include the kappa, lambda, alpha, gamma, delta, epsilon and mu constant regions, as well as a myriad of immunoglobulin variable regions. Light chains are classified as either kappa or lambda. Light chains comprise a variable light ($V_L$) and a constant light ($C_L$) domain. Heavy chains are classified as gamma, mu, alpha, delta, or epsilon, which in turn define the immunoglobulin classes IgG, IgM, IgA, IgD and IgE, respectively. Heavy chains comprise variable heavy ($V_H$), constant heavy 1 (CH1), hinge, constant heavy 2 (CH2), and constant heavy 3 (CH3) domains. The IgG heavy chains are further sub-classified based on their sequence variation, and the subclasses are designated IgG1, IgG2, IgG3 and IgG4.

Antibodies can be further broken down into two pairs of a light and heavy domain. The paired $V_L$ and $V_H$ domains each comprise a series of seven subdomains: framework region 1 (FR1), complementarity determining region 1 (CDR1), framework region 2 (FR2), complementarity determining region 2 (CDR2), framework region 3 (FR3), complementarity determining region 3 (CDR3), framework region 4 (FR4) which constitute the antibody-antigen recognition domain.

A chimeric antibody may be made by splicing the genes from a monoclonal antibody of appropriate antigen specificity together with genes from a second human antibody of appropriate biologic activity. More particularly, the chimeric antibody may be made by splicing the genes encoding the variable regions of an antibody together with the constant region genes from a second antibody molecule. This method is used in generating a humanized monoclonal antibody wherein the complementarity determining regions are mouse, and the framework regions are human thereby decreasing the likelihood of an immune response in human patients treated with the antibody (U.S. Pat. Nos. 4,816,567, 4,816,397, 5,693,762; 5,585,089; 5,565,332 and 5,821,337 which are incorporated herein by reference in their entirety).

An antibody suitable for use in the present invention may be obtained from natural sources or produced by hybridoma, recombinant or chemical synthetic methods, including modification of constant region functions by genetic engineering techniques (U.S. Pat. No. 5,624,821). The antibody of the present invention may be of any isotype, but is preferably human IgG1.

Antibodies exist for example, as intact immunoglobulins or can be cleaved into a number of well-characterized fragments produced by digestion with various peptidases, such as papain or pepsin. Pepsin digests an antibody below the disulfide linkages in the hinge region to produce a F(ab)'2 fragment of the antibody which is a dimer of the Fab composed of a light chain joined to a VH—CH1 by a disulfide bond. The F(ab)'2 may be reduced under mild conditions to break the disulfide linkage in the hinge region thereby converting the F(ab)'2 dimer to a Fab' monomer. The Fab' monomer is essentially an Fab with part of the hinge region. See Paul, ed., 1993, Fundamental Immunology, Third Edition (New York: Raven Press), for a detailed description of epitopes, antibodies and antibody fragments. One of skill in the art will recognize that such Fab' fragments may be synthesized de novo either chemically or using recombinant DNA technology. Thus, as used herein, the term antibody fragments includes antibody fragments produced by the modification of whole antibodies or those synthesized de novo.

As used herein, an antibody can also be a single-chain antibody (scFv), which generally comprises a fusion polypeptide consisting of a variable domain of a light chain fused via a polypeptide linker to the variable domain of a heavy chain.

The invention also encompasses the use of a polyclonal population of anti-TSG101 antibodies for inhibiting or reducing viral infection. As used herein, a polyclonal population of anti-TSG101 antibodies of the present invention refers to a population of anti-TSG101 antibodies, which comprises a plurality of different anti-TSG101 antibodies each having a different binding specificity. In one embodiment, the population of anti-TSG101 antibodies comprises antibodies that bind a C-terminal region of a TSG101 protein. In a preferred embodiment, the population of anti-TSG101 antibodies comprises antibodies that bind one or more epitopes comprised in the amino acid region QLRALMQKARKTAGLSDLY (SEQ ID NO:3). In another embodiment, the population of anti-TSG101 antibodies comprises antibodies that bind an N-terminal region of a TSG101 protein. In a specific embodiment, the population of anti-TSG101 antibodies comprises antibodies that bind one or more epitopes comprised in the amino acid region VRETVNVITLYKDLKPVL (SEQ ID NO:2).

Preferably, the plurality of anti-TSG101 antibodies of the polyclonal population includes specificities for different epitopes of TSG101 protein. In preferred embodiments, at least 90%, 75%, 50%, 20%, 10%, 5%, or 1% of anti-TSG101 antibodies in the polyclonal population target the desired epitopes. In other preferred embodiments, the proportion of any single anti-TSG101 antibody in the polyclonal population does not exceed 90%, 50%, or 10% of the population. The polyclonal population comprises at least 2 different anti-TSG101 antibodies with different specificities. More preferably, the polyclonal population comprises at least 10 different anti-TSG101 antibodies. Most preferably, the polyclonal population comprises at least 100 different anti-TSG101 antibodies with different specificities.

5.2. Production of Anti-TSG101 Antibodies

TSG101 protein or a fragment thereof can be used to raise antibodies which bind TSG101 protein. Such antibodies include but are not limited to polyclonal, monoclonal, chimeric, single chain, Fab fragments, and an Fab expression library. In a preferred embodiment, anti C-terminal TSG101 antibodies are raised using an appropriate C-terminal fragment of a TSG101 protein. Such antibodies are useful in inhibiting viral production.

5.2.1. Production of Monoclonal Anti-TSG101 Antibodies

Antibodies can be prepared by immunizing a suitable subject with a TSG101 protein or a fragment thereof as an immunogen. The antibody titer in the immunized subject can be monitored over time by standard techniques, such as with an enzyme linked immunosorbent assay (ELISA) using immobilized polypeptide. If desired, the antibody molecules can be isolated from the mammal (e.g., from the blood) and further purified by well-known techniques, such as protein A chromatography to obtain the IgG fraction. In one embodiment, an anti-N terminal TSG101 antibody (also referred to as anti-TSG101 antibody "C") is raised using an N-terminal fragment of the human TSG101 protein: VRETVNVITLYKDLKPVL (SEQ ID NO:2). In another embodiment, an anti-C terminal TSG101 antibody (also referred to as anti-TSG101 antibody "E") is raised using a C-terminal fragment of the human TSG101 protein: QLRALMQKARKTAGLSDLY (SEQ ID NO:3).

At an appropriate time after immunization, e.g., when the specific antibody titers are highest, antibody-producing cells can be obtained from the subject and used to prepare monoclonal antibodies by standard techniques, such as the hybridoma technique originally described by Kohler and Milstein (1975, Nature 256:495-497), the human B cell hybridoma technique by Kozbor et al. (1983, Immunol. Today 4:72), the EBV-hybridoma technique by Cole et al. (1985, Monoclonal Antibodies and Cancer Therapy, Alan R. Liss, Inc., pp. 77-96) or trioma techniques. The technology for producing hybridomas is well known (see Current Protocols in Immunology, 1994, John Wiley & Sons, Inc., New York, N.Y.). Hybridoma cells producing a monoclonal antibody of the invention are detected by screening the hybridoma culture supernatants for antibodies that bind the polypeptide of interest, e.g., using a standard ELISA assay.

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies. For example, the monoclonal antibodies may be made using the hybridoma method first described by Kohler et al., 1975, Nature, 256:495, or may be made by recombinant DNA methods (U.S. Pat. No. 4,816,567). The term "monoclonal antibody" as used herein also indicates that the antibody is an immunoglobulin.

In the hybridoma method of generating monoclonal antibodies, a mouse or other appropriate host animal, such as a hamster, is immunized as hereinabove described to elicit lymphocytes that produce or are capable of producing antibodies that will specifically bind to the protein used for immunization (see, e.g., U.S. Pat. No. 5,914,112, which is incorporated herein by reference in its entirety).

Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)). The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA.

Human myeloma and mouse-human heteromyeloma cell lines also have been described for the production of human monoclonal antibodies (Kozbor, 1984, J. Immunol., 133:3001; Brodeur et al., Monoclonal Antibody Production Techniques and Applications, pp. 51-63 (Marcel Dekker, Inc., New York, 1987)). Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immuno-absorbent assay (ELISA). The binding affinity of the monoclonal antibody can, for example, be determined by the Scatchard analysis of Munson et al., 1980, Anal. Biochem., 107:220.

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103, Academic Press, 1986). Suitable culture media for this purpose include, for example, D-MEM or RPMI-1640 medium. In addition, the hybridoma cells may be grown in vivo as ascites tumors in an animal. The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Alternative to preparing monoclonal antibody-secreting hybridomas, a monoclonal antibody directed against a TSG101 protein or a fragment thereof can be identified and isolated by screening a recombinant combinatorial immunoglobulin library (e.g., an antibody phage display library) with the TSG101 protein or the fragment. Kits for generating and screening phage display libraries are commercially available (e.g., Pharmacia Recombinant Phage Antibody System, Catalog No. 27-9400-01; and the Stratagene antigen SurfZAP™ Phage Display Kit, Catalog No. 240612). Additionally, examples of methods and reagents particularly amenable for use in generating and screening antibody display library can be found in, for example, U.S. Pat. Nos. 5,223,409 and 5,514,548; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al., 1991, Bio/Technology 9:1370-1372; Hay et al., 1992, Hum. Antibod. Hybridomas 3:81-85; Huse et al., 1989, Science 246:1275-1281; Griffiths et al., 1993, EMBO J. 12:725-734.

In addition, techniques developed for the production of "chimeric antibodies" (Morrison, et al., 1984, Proc. Natl. Acad. Sci., 81, 6851-6855; Neuberger, et al., 1984, Nature 312, 604-608; Takeda, et al., 1985, Nature, 314, 452-454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entirety.)

Humanized antibodies are antibody molecules from non-human species having one or more complementarity determining regions (CDRs) from the non-human species and a framework region from a human immunoglobulin molecule. (see e.g., U.S. Pat. No. 5,585,089, which is incorporated herein by reference in its entirety.) Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Patent No. 4,816,567 and 5,225,539; European Patent Application 125,023; Better et al., 1988, Science 240:1041-1043; Liu et al., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Canc. Res. 47:999-1005; Wood et al., 1985, Nature 314:446-449; Shaw et al., 1988, J. Natl. Cancer Inst. 80:1553-1559; Morrison 1985, Science 229:1202-1207; Oi et al., 1986, Bio/Techniques 4:214; Jones et al., 1986, Nature 321:552-525; Verhoeyan et al., 1988, Science 239:1534; and Beidler et al., 1988, J. Immunol. 141: 4053-4060.

Complementarity determining region (CDR) grafting is another method of humanizing antibodies. It involves reshaping murine antibodies in order to transfer full antigen specificity and binding affinity to a human framework (Winter et al. U.S. Pat. No. 5,225,539). CDR-grafted antibodies have been successfully constructed against various antigens, for example, antibodies against IL-2 receptor as described in Queen et al., 1989 (Proc. Natl. Acad. Sci. USA 86:10029); antibodies against cell surface receptors-CAMPATH as described in Riechmann et al. (1988, Nature, 332:323; antibodies against hepatitis B in Cole et al. (1991, Proc. Natl. Acad. Sci. USA 88:2869); as well as against viral antigens-respiratory syncitial virus in Tempest et al. (1991, Bio-Technology 9:267). CDR-grafted antibodies are generated in which the CDRs of the murine monoclonal antibody are grafted into a human antibody. Following grafting, most antibodies benefit from additional amino acid changes in the framework region to maintain affinity, presumably because framework residues are necessary to maintain CDR conformation, and some framework residues have been demonstrated to be part of the antigen binding site. However, in order to preserve the framework region so as not to introduce any antigenic site, the sequence is compared with established germline sequences followed by computer modeling.

Completely human antibodies are particularly desirable for therapeutic treatment of human patients. Such antibodies can be produced using transgenic mice which are incapable of expressing endogenous immunoglobulin heavy and light chain genes, but which can express human heavy and light chain genes. The transgenic mice are immunized in the normal fashion with a TSG101 protein.

Monoclonal antibodies directed against a TSG101 protein can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see e.g., U.S. Pat. No. 5,625,126; U.S. Pat. No. 5,633,425; U.S. Pat. No. 5,569,825; U.S. Pat. No. 5,661,016; and U.S. Pat. No. 5,545,806. In addition, companies such as Abgenix, Inc. (Freemont, Calif., see, for example, U.S. Pat. No. 5,985,615) and Medarex, Inc. (Princeton, N.J.), can be engaged to provide human antibodies directed against a TSG101 protein or a fragment thereof using technology similar to that described above.

Completely human antibodies which recognize and bind a selected epitope can be generated using a technique referred to as "guided selection." In this approach a selected non-human monoclonal antibody, e.g., a mouse antibody, is used to guide the selection of a completely human antibody recognizing the same epitope (Jespers et al., 1994, Bio/technology 12:899-903).

A pre-existing anti-TSG101 antibody can be used to isolate additional antigens of the pathogen by standard techniques, such as affinity chromatography or immunoprecipitation for use as immunogens. Moreover, such an antibody can be used to detect the protein (e.g., in a cellular lysate or cell supernatant) in order to evaluate the abundance and pattern of expression of TSG101 protein. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include 125I, 131I, 35S or 3H.

5.2.2. Production of Polyclonal Anti-TSG101 Antibodies

The anti-TSG101 antibodies can be produced by immunization of a suitable animal, such as but are not limited to mouse, rabbit, and horse.

An immunogenic preparation comprising a TSG101 protein or a fragment thereof are used to prepare antibodies by immunizing a suitable subject (e.g., rabbit, goat, mouse or other mammal). An appropriate immunogenic preparation can contain, for example, recombinantly expressed or chemically synthesized TSG101 peptide or polypeptide. The preparation can further include an adjuvant, such as Freund's complete or incomplete adjuvant, or similar immunostimulatory agent.

A fragment of a TSG101 protein suitable for use as an immunogen comprises at least a portion of the TSG101 protein that is 8 amino acids, more preferably 10 amino acids and more preferably still, 15 amino acids long.

The invention also provides chimeric or fusion TSG101 polypeptides for use as immunogens. As used herein, a "chimeric" or "fusion" TSG101 polypeptides comprises all or part of a TSG101 polypeptide operably linked to a heterologous polypeptide. Within the fusion TSG101 polypeptide, the term "operably linked" is intended to indicate that the TSG101 polypeptide and the heterologous polypeptide are fused in-frame to each other. The heterologous polypeptide can be fused to the N-terminus or C-terminus of the TSG101 polypeptide.

One useful fusion TSG101 polypeptide is a GST fusion TSG101 polypeptide in which the TSG101 polypeptide is fused to the C-terminus of GST sequences. Such fusion TSG101 polypeptides can facilitate the purification of a recombinant TSG101 polypeptide.

In another embodiment, the fusion TSG101 polypeptide contains a heterologous signal sequence at its N-terminus so that the TSG101 polypeptide can be secreted and purified to high homogeneity in order to produce high affinity antibodies. For example, the native signal sequence of an immunogen can be removed and replaced with a signal sequence from another protein. For example, the gp67 secretory sequence of the baculovirus envelope protein can be used as a heterologous signal sequence (Current Protocols in Molecular Biology, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal and the protein A secretory signal (Pharmacia Biotech; Piscataway, N.J.).

In yet another embodiment, the fusion TSG101 polypeptide is an immunoglobulin fusion protein in which all or part of a TSG101 polyetide is fused to sequences derived from a member of the immunoglobulin protein family. The immunoglobulin fusion proteins can be used as immunogens to produce antibodies directed against the TSG101 polypetide in a subject.

Chimeric and fusion TSG101 polypeptide can be produced by standard recombinant DNA techniques. In one embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (e.g., Ausubel et al., supra). Moreover, many expression vectors are commercially available that already encode a fusion domain (e.g., a GST polypeptide). A nucleic acid encoding an immunogen can be cloned into such an expression vector such that the fusion domain is linked in-frame to the polypeptide.

The TSG101 immunogenic preparation is then used to immunize a suitable animal. Preferably, the animal is a specialized transgenic animal that can secret human antibody. Non-limiting examples include transgenic mouse strains which can be used to produce a polyclonal population of antibodies directed to a specific pathogen (Fishwild et al., 1996, Nature Biotechnology 14:845-851; Mendez et al., 1997, Nature Genetics 15:146-156). In one embodiment of the invention, transgenic mice that harbor the unrearranged human immunoglobulin genes are immunized with the target immunogens. After a vigorous immune response against the immunogenic preparation has been elicited in the mice, the blood of the mice are collected and a purified preparation of human IgG molecules can be produced from the plasma or serum. Any method known in the art can be used to obtain the purified preparation of human IgG molecules, including but is not limited to affinity column chromatography using anti-human IgG antibodies bound to a suitable column matrix. Anti-human IgG antibodies can be obtained from any sources known in the art, e.g., from commercial sources such as Dako Corporation and ICN. The preparation of IgG molecules produced comprises a polyclonal population of IgG molecules that bind to the immunogen or immunogens at different degree of affinity. Preferably, a substantial fraction of the preparation are IgG molecules specific to the immunogen or immunogens. Although polyclonal preparations of IgG molecules are described, it is understood that polyclonal preparations comprising any one type or any combination of different types of immunoglobulin molecules are also envisioned and are intended to be within the scope of the present invention.

A population of antibodies directed to a TSG101 protein can be produced from a phage display library. Polyclonal antibodies can be obtained by affinity screening of a phage display library having a sufficiently large and diverse population of specificities with a TSG101 protein or a fragment thereof. Examples of methods and reagents particularly amenable for use in generating and screening antibody display library can be found in, for example, U.S. Pat. Nos. 5,223,409 and 5,514,548; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al., 1991, Bio/Technology 9:1370-1372; Hay et al., 1992, Hum. Antibod. Hybridomas 3:81-85; Huse et al., 1989, Science 246:1275-1281; Griffiths et al., 1993, EMBO J. 12:725-734. A phage display library permits selection of desired antibody or antibodies from a very large population of specificities. An additional advantage of a phage display library is that the nucleic acids encoding the selected antibodies can be obtained conveniently, thereby facilitating subsequent construction of expression vectors.

In other preferred embodiments, the population of antibodies directed to a TSG101 protein or a fragment thereof is produced by a method using the whole collection of selected displayed antibodies without clonal isolation of individual members as described in U.S. Pat. No. 6,057,098, which is incorporated by reference herein in its entirety. Polyclonal antibodies are obtained by affinity screening of a phage display library having a sufficiently large repertoire of specificities with, e.g., an antigenic molecule having multiple epitopes, preferably after enrichment of displayed library members that display multiple antibodies. The nucleic acids encoding the selected display antibodies are excised and amplified using suitable PCR primers. The nucleic acids can be purified by gel electrophoresis such that the full length nucleic acids are isolated. Each of the nucleic acids is then inserted into a suitable expression vector such that a population of expression vectors having different inserts is obtained. The population of expression vectors is then expressed in a suitable host.

5.2.3. Identifying Anti-TSG101 Antibodies that Inhibit Viral Production

The invention provides a method for identifying anti-TSG101 antibodies that can be used to inhibit or reduce viral budding. In one embodiment, the invention provides a method for determining the effect of anti-TSG101 antibodies on viral infections using a retroviral infection assay. A murine leukemia virus (MLV) derived vector which contains an *E. coli* lacZ gene expressed from the long terminal repeat (LTR) promoter(pBMN-Z-I-Neo) is transfected into an amphotropic murine leukemia retroviral packaging cell line derived from 293 cells (Phoenix A, ATCC). Retroviruses produced by the Phoenix A helper cells are collected and used to infect a mouse N2A cells (ATCC). Anti-TSG101 antibodies are added to 293 helper cells 24 hours after the transfection of the MLV vector. The effectiveness of TSG101 antibodies on viral production is determined by the efficiency of viral supernatant to infect the target cells (N2A). The infection of N2A cells is then determined by cellular staining of β-galactosidase activity (positive cells are stained blue, shown as dark spots in FIG. 2).

Typically, phoenix A cells are seeded on poly-D-lysine coated 6-well plate a day before transfection. Four microgram of pBMN-Z-I-Neo is then transfected into each well in the presence of 12 ul of Lipofectamine 2000 (Invitrogen). Twenty-four hours post-transfection, media are replaced with 1 ml/well of fresh media containing trichostatin A (3 uM) and 5 or 10 ug of proper anti-TSG101 antibodies. 24 to 48 hours later, viral supernatants are collected, filtered with 0.2 um filters, and 1 ml of viral supernatant is mixed with 1 ml of fresh media containing polybrene (10 ug/ml), and then is used to infect one well of N2a cells. 48 hours post-infection, N2a cells are fixed and stained with X-Gal as described in the β-Gal staining kit (Invitrogen). Results are documented by digital images. Preferably, anti-TSG101 antibodies that reduce viral production by at least 10%, 20%, 50%, 70% or 90% are identified.

Figure 2:
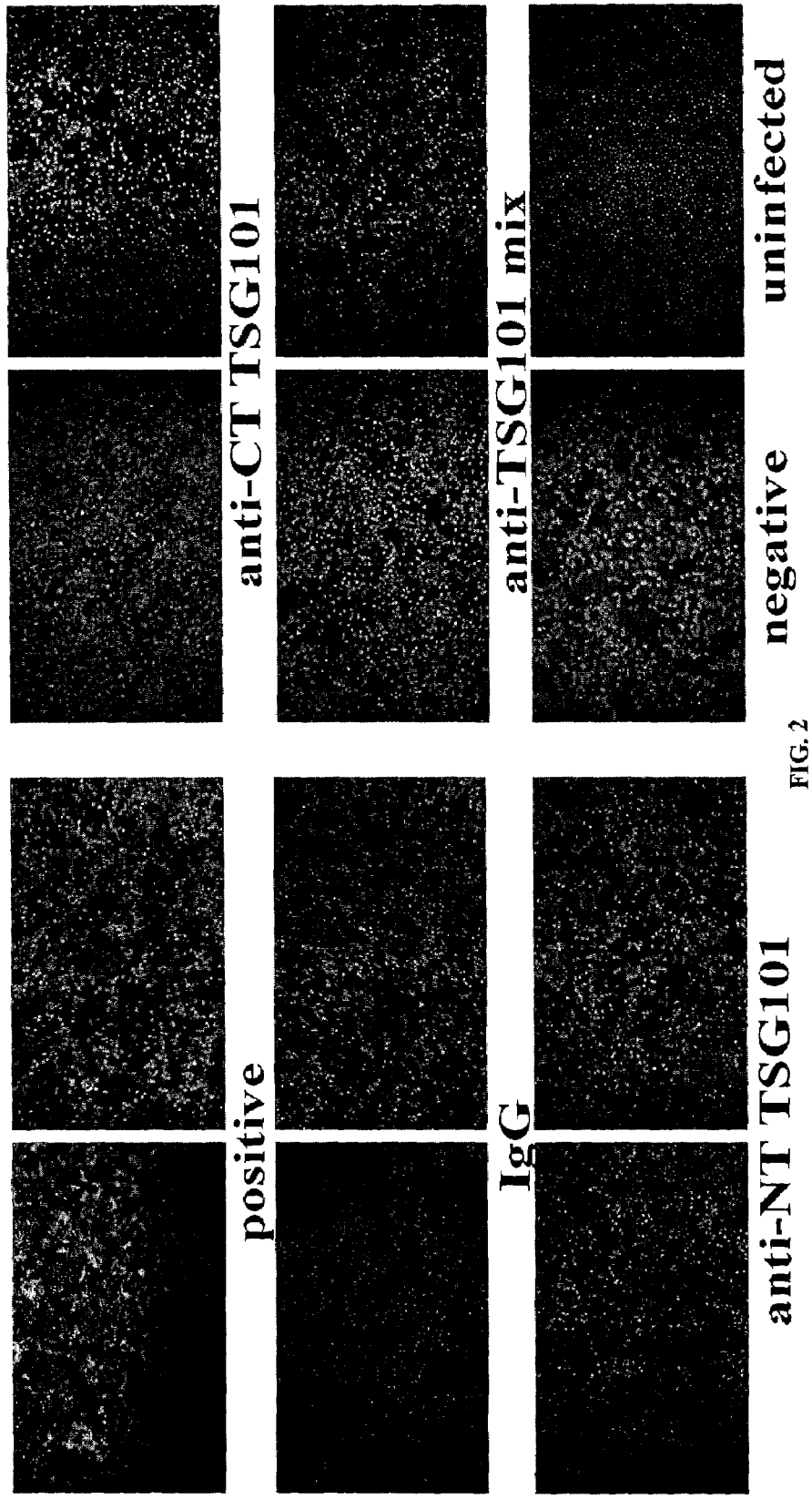
Figure 3:
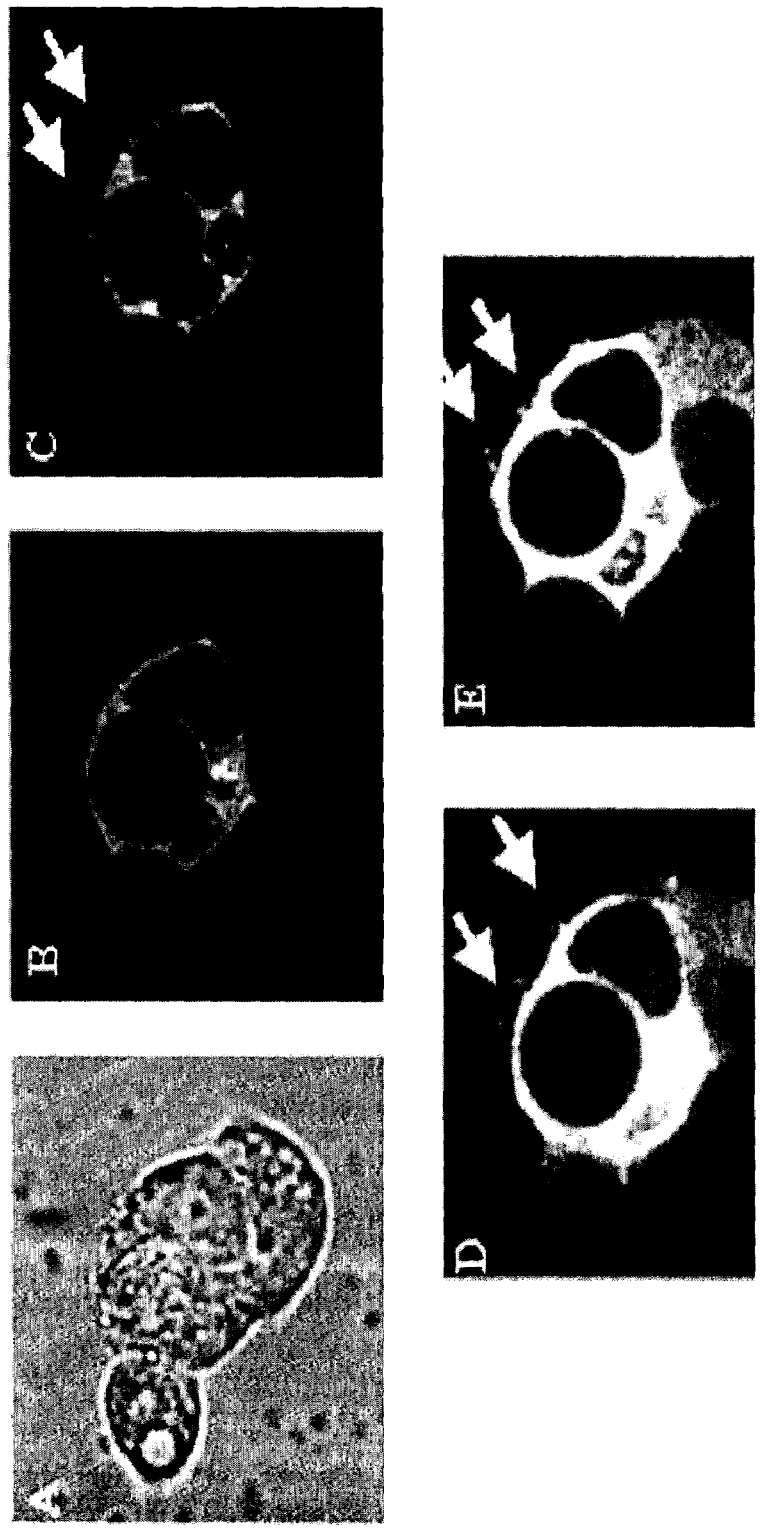

In the following exemplery experiments, the two anti-TSG101 antibodies "C" and "E" are tested for their effect on viral infection. Rabbit IgG is used as non-specific antibody control. More than 10 independent experiments are performed, and representative results are shown in FIG. 2. Phoenix helper cells without treatment of antibody (positive control) showed efficient production of retroviruses, and infection of N2A target cells (left top panel); Rabbit IgG had no effect (left middle panel). The anti-TSG101 antibody "C" reduced viral production by about 20%-60% (left bottom panel). The anti-TSG101 antibody "E" reduced viral production by about 50-70% (right top panel). A mixture of anti-C-terminal and anti-N-terminal antibodies give similar results as the anti-C terminal antibody alone (Right middle panel). N2a cells that are not infected by viruses only showed minimal background staining (right bottom panel).

In another embodiment, anti-TSG101 antibodies that can be used to inhibit or reduce viral budding are identified based on their binding to cell surface TSG101, e.g., in a human CD4+ human T cell line H9 transfected with HIV (designated as H9ΔBgl). H9ΔBgl cells are human CD4+ T lymphocytes transfected with an envelop-defective HIV construct (deletion of a Bgl II fragment of HIV genome). The stably transfected H9ΔBgl cells produce a non-infectious form of HIV due to the defective HIV envelop, hence cannot infect other H9ΔBgl cells in the culture. In one embodiment, the untransfected H9 cells are used as control. Anti-TSG101 antibodies that bind to H9ΔBgl but not the untransfected H9 cells are identified as the antibodies that can be used to inhibit or reduce viral budding.

In a preferred embodiment, binding of an anti-TSG101 antibody to cell surface TSG101 in HIV producing cells (e.g., H9ΔBgl) and control H9 cells is identified by Fluorescence Activated Cell Sorting (FACS). In one embodiment, both H9ΔBgl and H9 cells are fixed, incubated with anti-TSG101 antibodies, and then stained with a fluorescence labeled secondary antibody. The immuno-stained cells are then analyzed by FACS.

In another embodiment, a HIV-1 viral production assay is used to further examine the inhibitory effect of TSG101 on retroviral production. The HIV-1 vector pNL4-3 is transfected into 293T cells. 24 hours after transfaction, an anti-TSG101 antibody and, optionally, a non-specific control antibody are added respectively into the cell cultures. After additional 24 hours incubation, cell lysates are extracted, cell culture supernatants are collected and HIV-1 virions are purified, e.g., by sucrose gradients. Both cell lysates and purified virions are analyzed by Western blot using, e.g., anti-HIV-1 antibodies such as anti-p55 and/or anti-p24 antibodies. Anti-TSG101 antibody that exhibit significant inhibition of HIV-1 virion release (e.g., more than 40%, 50%, 60%, 70%, or 80% inhibition by density tracing of the Western blots) can be identified.

In still another embodiment, the effect of an anti-TSG101 antibody on HIV release is evaluated using a HIV release assay based on H9ΔBgl cells. HIV release from H9ΔBgl cells can be directly measured by HIV p24 ELISA of cell culture supernatant. In one embodiment, a plurality of different concentrations of an anti-TSG101 antibody is incubated respectively with H9ΔBgl cells. In one embodiment, a control antibody (e.g., rabbit IgG at the same concentrations) is also incubated respectively with H9ΔBgl cells. 48 hours after antibody addition, culture supernatants are collected for HIV p24 ELISA. Effect of the anti-TSG101 antibody for inhibition of viral release is then determined by comparing data of the anti-TSG101 antibody with the data of the corresponding control antibody.

In still another embodiment, the effect of an anti-TSG110 antibody on HIV infectivity following viral release is determined. In one embodiment, HIV supernatants from Jurkat cells are used to infect MAGI cells in the presence of an anti-TSG101 antibody. Rabbit IgG can be used as controls. The anti-TSG101 antibody's effect on HIV infectivity is determined by comparing with the control.

5.3. Uses of Anti-TSG101 Antibodies for Treatment of Viral Infections

TSG101 antibodies are effective in inhibiting viral production. The invention therefore provides a method of treating viral infections, including HIV infection, using TSG101 antibodies, e.g., anti-C-terminal TSG101 antibodies.

5.3.1. Viral Infections

Diseases or disorders that can be treated or prevented by the use of an anti-TSG101 antibody of the present invention include, but are not limited to, those caused by a ritrovirus, rhabdovirus, or filovirus, hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, hantavirus, coxsachie virus, mumps virus, measles virus, rubella virus, polio virus, human immunodeficiency virus type I (HIV-I), and human immunodeficiency virus type II (HIV-II), any picomaviridae, enteroviruses, caliciviridae, any of the Norwalk group of viruses, togaviruses, alphaviruses, flaviviruses, such as Dengue virus, coronaviruses, rabies virus, Marburg viruses, Ebola viruses, parainfluenza virus, orthomyxoviruses, bunyaviruses, arenaviruses, reoviruses, rotaviruses, orbiviruses, human T cell leukemia virus type I, human T cell leukemia virus type II, simian immunodeficiency virus, lentiviruses, polyomaviruses, parvoviruses, Epstein-Barr virus, human herpesvirus-6, cercopithecine herpes virus 1 (B virus), and poxviruses.

Additional diseases or disorders that can be treated or prevented by the use of an anti-TSG101 antibody of the present invention include, but are not limited to, those caused by influenza virus, human respiratory syncytial virus, pseudorabies virus, pseudorabies virus II, swine rotavirus, swine parvovirus, bovine viral diarrhea virus, Newcastle disease virus h, swine flu virus, swine flu virus, foot and mouth disease virus, hog colera virus, swine influenza virus, African swine fever virus, infectious bovine rhinotracheitis virus, infectious laryngotracheitis virus, La Crosse virus, neonatal calf diarrhea virus, Venezuelan equine encephalomyelitis virus, punta toro virus, murine leukemia virus, mouse mammary tumor virus, equine influenza virus or equine herpesvirus, bovine respiratory syncytial virus or bovine parainfluenza virus.

5.3.2 Methods of using Anti-TSG101 Antibodies For Inhibiting Viral Release

In one embodiment, the present invention provides methods of using anti-TSG101 antibodies, preferably anti-C-terminal TSG101 antibodies, in inhibiting or reducing viral budding, such as HIV-1 budding, from infected mammalian cells. In the methods of the invention, one or more anti-TSG101 antibodies are allowed to contact an infected cell. The anti-TSG101 antibodies binds to the TSG101 protein on the surface of the infected cell. The binding of the anti-TSG101 antibodies inhibits or reduces the release, or budding, of viral particles from the cell.

In another embodiment, the present invention thus also provides methods using anti-TSG101 antibodies, preferably anti-C-terminal TSG101 antibodies, for treating infection by an enveloped virus, e.g., HIV-1, in a mammal, e.g., a human. In the methods of the invention, one or more anti-TSG101 antibodies can be administered to an mammal, e.g., a human, infected by the virus. After administration, the anti-TSG101 antibodies bind to TSG101 protein on the surface of an infected cell and inhibiting viral budding from the infected cell.

In still another embodiment of the invention, the anti-TSG101 antibodies, preferably anti-C-terminal TSG101 antibodies are used in conjunction with one or more other therapeutic anti-viral drugs. In such combined therapies, the anti-TSG101 antibodies can be administered before, at the same time, or after the administration of the therapeutic drugs. The time intervals between the administration of the anti-TSG101 antibodies and the therapeutic drugs can be determined by routine experiments that are familiar to one skilled in the art.

In still another embodiment, the present invention provides a method for treatment of viral infection using an anti-TSG101 antibody, e.g., an anti-C-terminal TSG101 antibody, that belongs to an isotype that is capable of mediating the lysis of infected cells to which the anti-TSG101 antibody is bound.

In a preferred embodiment, the anti-TSG101 antibody belongs to an isotype that binds a growth factor receptor and activates serum complement and/or mediates antibody dependent cellular cytotoxicity (ADCC) by activating effector cells, e.g., macrophages. In another preferred embodiment, the isotype is IgG1, IgG2a, IgG3 or IgM.

The dosage of the anti-TSG101 antibodies can be determined by routine experiments that are familiar to one skilled in the art. The effects or benefits of administration of the anti-TSG0 1 antibodies can be evaluated by any methods known in the art.

5.3.3 Methods of Using Anti-TSG101 Antibodies for Delivering Therapeutic and/or Diagnostic Agents The invention provides methods and compositions for using anti-TSG101 antibodies for delivering therapeutic and/or diagnostic agents to viral infected cells.

Infected cells can be targeted and killed using anti-TSG101 antibody-drug conjugates. For example, an anti-TSG101 antibody may be conjugated to a therapeutic moiety such as a cytotoxin, e.g., a cytostatic or cytocidal agent, or a radioactive metal ion. Antibody-drug conjugates can be prepared by method known in the art (see, e.g., Immunoconjugates, Vogel, ed. 1987; Targeted Drugs, Goldberg, ed. 1983; Antibody Mediated Delivery Systems, Rodwell, ed. 1988). Therapeutic drugs, such as but are not limited to, paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof, can be conjugated to anti-TSG101 antibodies of the invention. Other therapeutic agents that can be conjugated to anti-TSG101 antibodies of the invention include, but are not limited to, antimetabolites, e.g., methotrexate, 6-mercaptopurine, 6-thioguanine, cytarabine, 5-fluorouracil decarbazine; alkylating agents, e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin; anthracyclines, e.g., daunorubicin (daunomycin) and doxorubicin; antibiotics, e.g., dactinomycin (actinomycin), bleomycin, mithramycin, anthramycin (AMC); and anti-mitotic agents, e.g., vincristine and vinblastine. The therapeutic agents that can be conjugated to anti-TSG101 antibodies of the invention may also be a protein or polypeptide possessing a desired biological activity. Such proteins may include, for example, a toxin such as abrin, ricin A, pseudomonas exotoxin, or diphtheria toxin.

The drug molecules can be linked to the anti-TSG101 antibody via a linker. Any suitable linker can be used for the preparation of such conjugates. In some embodiments, the linker can be a linker that allows the drug molecules to be released from the conjugates in unmodified form at the target site.

The antibodies can also be used diagnostically to, for example, monitor the progression of a viral infection as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See generally U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include fluorescent proteins, e.g., green fluorescent protein (GFP), umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{111}In$, $^{117}Lu$, $^{90}Y$ or $^{99}Tc$.

Techniques for conjugating therapeutic moieties to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982); each of which is incorporated herein by reference.

Alternatively, an antibody can be conjugated to a second antibody to form an antibody heteroconjugate as described by Segal in U.S. Pat. No. 4,676,980, which is incorporated herein by reference.

5.3.4. Detection of Viral Infected Cells

Antibodies or labeled antibodies directed against a Tsg101 protein, e.g., an N-terminal region or a C-terminal region of a TSG101 protein, may also be used as diagnostics and prognostics of viral infection, e.g., by detecting the presence of TSG101 protein on cell surface. Such diagnostic methods, may also be used to detect abnormalities in the level of Tsg101 gene expression, or abnormalities in the structure and/or temporal, tissue, cellular, or subcellular location of a Tsg101 protein.

The tissue or cell type to be analyzed may include those which are known, or suspected, to be infected by a virus. The protein isolation methods employed herein may, for example, be such as those described in Harlow and Lane (Harlow, E. and Lane, D., 1988, "Antibodies: A Laboratory Manual", Cold Spring Harbor Laboratory Press, Cold Spring Harbor, N.Y.), which is incorporated herein by reference in its entirety. The isolated cells can be derived from cell culture or from a patient. The analysis of cell taken from culture may be a necessary step in the assessment of cells to be used as part of a cell-based gene therapy technique or, alternatively, to test the effect of compounds on the expression of the Tsg101 gene.

Preferred diagnostic methods for the detection of Tsg101 fragments or conserved variants or peptide fragments thereof, may involve, for example, immunoassays wherein the Tsg101 fragments or conserved variants or peptide fragments are detected by their interaction with an anti-Tsg101 fragment-specific antibody.

For example, antibodies, or fragments of antibodies, such as those described above useful in the present invention may be used to quantitatively or qualitatively detect infected cells by the presence of Tsg101 fragments or conserved variants or peptide fragments thereof on their surfaces. This can be accomplished, for example, by immunofluorescence techniques employing a fluorescently labeled antibody (see below, this Section) coupled with light microscopic, flow cytometric, or fluorimetric detection. Such techniques are especially useful in viral infection where Tsg101 fragments are recruited to the cell surface during the viral budding process.

The antibodies (or fragments thereof) useful in the present invention may, additionally, be employed histologically, as in immunofluorescence or immunoelectron microscopy, for in situ detection of Tsg101 fragments or conserved variants or peptide fragments thereof. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the Tsg101 fragment, or conserved variants or peptide fragments, but also its distribution in the examined tissue. Using the present invention, those of ordinary skill will readily perceive that any of a wide variety of histological methods (such as staining procedures) can be modified in order to achieve such in situ detection.

Immunoassays for Tsg101 fragments or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of identifying Tsg101 fragments or conserved variants or peptide fragments thereof, and detecting the bound antibody by any of a number of techniques well-known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled Tsg101 protein specific antibody. The solid phase support may then be washed with the buffer a second time to remove unbound antibody. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tub, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-Tsg101 fragment antibody may be determined according to well known methods. Those skilled in the art will be able to determine operative and optimal assay conditions for each determination by employing routine experimentation.

One of the ways in which the Tsg101 gene peptide-specific antibody can be detectably labeled is by linking the same to an enzyme and use in an enzyme immunoassay (EIA) (Voller, A., "The Enzyme Linked Immunosorbent Assay (ELISA)", 1978, Diagnostic Horizons 2:1-7, Microbiological Associates Quarterly Publication, Walkersville, Md.); Voller, A. et al., 1978, J. Clin. Pathol. 31:507-520; Butler, J. E., 1981, Meth. Enzymol. 73:482-523; Maggio, E. (ed.), 1980, Enzyme Immunoassay, CRC Press, Boca Raton, Fla.,; Ishikawa, E. et al., (eds.), 1981, Enzyme Immunoassay, Kgaku Shoin, Tokyo). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect Tsg101 peptides through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

5.3.5. Depletion of Viral Infected Cells In Vitro

The invention provides methods of depleting viral infected cells from non infected tissues and/or cells in vitro (or ex vivo). For example, the tissue obtained from a mammal for the in vitro depletion of viral infected cells from non infected cells can be blood or serum or other body fluid. In particular, the invention provides for methods of depleting viral infected cells by killing them or by separating them from non infected cells. In one embodiment, anti-TSG101 antibodies are combined, e.g., incubated, in vitro with tissues and/or cells obtained from a mammal, e.g., a human.

In one embodiment, a column containing a TSG101 antibody, e.g., an antibody that binds the N-Terminal or C-terminal region of a TSG101 protein, bound to a solid matrix is used to remove viral infected cells from a biological sample, e.g., blood or serum or other body fluid.

The anti-TSG101 antibodies used in the in vitro depletion of viral infected cells from tissues can be conjugated to detectable labels (e.g., various enzymes, fluorescent materials, luminescent materials, bioluminescent materials, and radioactive materials) or therapeutic agents (e.g., cytostatic and cytocidal agents), which are disclosed in section 5.3.2.

Anti-TSG101 antibodies conjugated to detectable substances can be utilized to sort viral infected cells from non infected cells by methods known to those of skill in the art. In one embodiment, viral infected cells are sorted using a fluorescence activated cell sorter (FACS). Fluorescence activated cell sorting (FACS) is a well-known method for separating particles, including cells, based on the fluorescent properties of the particles (Kamarch, 1987, Methods Enzymol, 151:150-165). Laser excitation of fluorescent moieties in the individual particles results in a small electrical charge allowing electromagnetic separation of positive and negative particles from a mixture.

In one embodiment, cells, e.g, blood cells, obtained a mammal, e.g., a human, are incubated with fluorescently labeled TSG101 specific antibodies for a time sufficient to allow the labeled antibodies to bind to the cells. In an alternative embodiment, such cells are incubated with TSG101 specific antibodies, the cells are washed, and the cells are incubated with a second labeled antibody that recognizes the TSG101 specific antibodies. In accordance with these embodiments, the cells are washed and processed through the cell sorter, allowing separation of cells that bind both antibodies to be separated from hybrid cells that do not bind both antibodies. FACS sorted particles may be directly deposited into individual wells of 96-well or 384-well plates to facilitate separation.

In another embodiment, magnetic beads can be used to separate viral infected cells from non infected cells. Viral infected cells may be sorted using a magnetic activated cell sorting (MACS) technique, a method for separating particles based on their ability to bind magnetic beads (0.5-100 nm diameter) (Dynal, 1995). A variety of useful modifications can be performed on the magnetic microspheres, including covalent addition of antibody which immunospecifically recognizes TSG101. A magnetic field is then applied, to physically manipulate the selected beads. The beads are then mixed with the cells to allow binding. Cells are then passed through a magnetic field to separate out viral infected cells.

5.3.6. Dose of Anti-TSG101 Antibodies

The dose can be determined by a physician upon conducting routine tests. Prior to administration to humans, the efficacy is preferably shown in animal models. Any animal model for an infectious disease known in the art can be used.

In general, for antibodies, the preferred dosage is 0.1 mg/kg to 100 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration are often possible. Modifications such as lipidation can be used to stabilize antibodies and to enhance uptake and tissue penetration (e.g., into the brain). A method for lipidation of antibodies is described by Cruikshank et al.,1997, J. Acquired Immune Deficiency Syndromes and Human Retrovirology 14:193.

As defined herein, a therapeutically effective amount of anti-TSG101 antibody (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an anti-TSG101 antibody can include a single treatment or, preferably, can include a series of treatments. In a preferred example, a subject is treated with an anti-TSG101 antibody in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of an anti-TSG101 antibody, used for treatment may increase or decrease over the course of a particular treatment. Changes in dosage may result and become apparent from the results of diagnostic assays as described herein.

It is understood that appropriate doses of anti-TSG101 antibody agents depends upon a number of factors within the ken of the ordinarily skilled physician, veterinarian, or researcher. The dose(s) of the anti-TSG101 antibody will vary, for example, depending upon the identity, size, and condition of the subject or sample being treated, further depending upon the route by which the composition is to be administered, if applicable, and the effect which the practitioner desires the anti-TSG101 antibody to have upon an infectious agent.

5.3.7. Pharmaceutical Formulation and Administration

The anti-TSG101 antibodies of the invention can be incorporated into pharmaceutical compositions suitable for administration. Such compositions typically comprise anti-TSG101 antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the anti-TSG101 antibody, use thereof in the compositions is contemplated. Supplementary anti-TSG101 antibodies can also be incorporated into the compositions.

A pharmaceutical composition of the invention is formulated to be compatible with its intended route of administration. Preferred routes of administration include subcutaneous and intravenous. Other examples of routes of administration include parenteral, intradermal, transdermal (topical), and transmucosal. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.) or phosphate buffered saline (PBS). In all cases, the composition must be sterile and should be fluid to the extent that the viscosity is low and the anti-TSG101 antibody is injectable. It must be stable under the conditions of manufacture and storage and must be preserved against the contaminating action of microorganisms such as bacteria and fungi.

The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the anti-TSG101 antibody (e.g., one or more anti-TSG101 antibodies) in the required amount in an appropriate solvent with one or a combination of ingredients enumerated above, as required, followed by filtered sterilization. Generally, dispersions are prepared by incorporating the anti-TSG101 antibody into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

In one embodiment, the anti-TSG101 antibodies are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811 which is incorporated herein by reference in its entirety.

It is advantageous to formulate parenteral compositions in dosage unit form for ease of administration and uniformity of dosage. Dosage unit form as used herein refers to physically discrete units suited as unitary dosages for the subject to be treated; each unit containing a predetermined quantity of anti-TSG101 antibody calculated to produce the desired therapeutic effect in association with the required pharmaceutical carrier. The specification for the dosage unit forms of the invention are dictated by and directly dependent on the unique characteristics of the anti-TSG101 antibody and the particular therapeutic effect to be achieved, and the limitations inherent in the art of compounding such an anti-TSG101 antibody for the treatment of individuals.

The pharmaceutical compositions can be included in a kit, in a container, pack, or dispenser together with instructions for administration.

5.4. TSG101 Vaccines and DNA Vaccines for Treatment and Prevention of Viral Infection The invention provides fragments of a TSG101 protein which can be used as vaccines to generate anti-TSG101 antibodies. The TSG101 protein fragment or polypeptide can be prepared by standard method known in the art. In one embodiment, the invention provides a fragment of a TSG101 protein not comprising the UEV domain of a TSG101 protein. In a specific embodiment, the invention provides a fragment of a human TSG101 protein, or its murine homolog, not comprising the UEV domain. In a preferred embodiment, the invention provides a fragment comprising the C-terminal region of a TSG101 protein. In another embodiment, the invention provides a fragment of a TSG101 protein comprising the coiled-coil domain of a TSG101 protein. In still another embodiment, the invention provides a fragment of a TSG101 protein comprising C-terminal domain of a TSG101 protein as described SEQ ID NO:3. The invention also provides any sequence that is at least 30%, 50%, 70%, 90%, or 95% homologous such fragments of a TSG101 protein. In some embodiments of the invention, the TSG101 protein fragments or polypeptides are at least 5, 10, 20, 50, 100 amino acids in length.

The invention also provides fragment of a TSG101 protein which is functionally equivalent to any TSG101 fragment described above. Such an equivalent TSG101 fragment may contain deletions, additions or substitutions of amino acid residues within the amino acid sequence encoded by the TSG101 protein gene sequences encoding the TSG101 protein but which result in a silent change, thus producing a functionally equivalent TSG101 protein fragment. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Functionally equivalent", as utilized herein, refers to a protein fragment capable of exhibiting a substantially similar in vivo activity as the endogenous TSG101 protein fragment.

The TSG101 peptide fragments of the invention may be produced by recombinant DNA technology using techniques well known in the art. Thus, methods for preparing the TSG101 polypeptides and peptides of the invention by expressing nucleic acid containing TSG101 gene sequences encoding the TSG101 polypeptide or peptide. Methods which are well known to those skilled in the art can be used to construct expression vectors containing TSG101 polypeptide coding sequences and appropriate transcriptional and translational control signals. These methods include, for example, in vitro recombinant DNA techniques, synthetic techniques, and in vivo genetic recombination. See, for example, the techniques described in Sambrook et al., 1989, supra, and Ausubel et al., 1989, supra. Alternatively, RNA capable of encoding TSG101 polypeptide sequences may be chemically synthesized using, for example, synthesizers. See, for example, the techniques described in "Oligonucleotide Synthesis", 1984, Gait, M. J. ed., IRL Press, Oxford, which is incorporated herein by reference in its entirety.

The TSG101 peptide can be used in combination with a suitable carrier and/or adjuvant, such as Freund's complete or incomplete adjuvant, or a similar immunostimulatory agent. An oil/surfactant based adjuvant comprising one or more surfactants combined with one or more non-metabolizable mineral oil or metabolizable oil, such as the Incomplete Seppic Adjuvant (Seppic, Paris, France), may be used. An Incomplete Seppic Adjuvant has comparable effect as Incomplete Freund's Adjuvant for antibody production, but induces lower inflammatory response.

The invention also provides portions of a tsg101 gene for use as DNA or RNA vaccine. The tsg101 gene fragments can also be used for producing any TSG101 protein fragment of the invention described above. In a preferred embodiment, the invention provides a fragment of a tsg101 gene comprising the nucleotide region encoding a fragment not comprising the UEV domain of a TSG101 protein. In a specific embodiment, the fragment of a TSG101 gene is a fragment of a human tsg101 gene, or its murine homolog. The invention also provides any sequence that is at least 30%, 50%, 70%, 90%, or 95% homologous to such fragments of a tsg101 gene. In some embodiments of the invention, the fragment of a tsg101 gene is at least 20, 25, 40, 60, 80, 100, 500, 1000 bases in length. Such sequences may be useful for production of TSG101 peptides.

The invention also provides (a) DNA vectors that contain any of the foregoing tsg101 coding sequences and/or their complements (i.e., antisense); (b) DNA expression vectors that contain any of the foregoing tsg101 coding sequences operatively associated with a regulatory element that directs the expression of the coding sequences; and (c) genetically engineered host cells that contain any of the foregoing TSG101 coding sequences operatively associated with a regulatory element that directs the expression of the coding sequences in the host cell for use in producing a TSG101 protein fragment of the invention. As used herein, regulatory elements include but are not limited to inducible and non-inducible promoters, enhancers, operators and other elements known to those skilled in the art that drive and regulate expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

In another embodiment, the present invention provides a naked DNA or RNA vaccine, and uses thereof. The tsg101 DNA fragment of the present invention described above can be administered as a vaccine to inhibit viral disease by eliciting anti-TSG101 antibodies of the invention. The DNA can be converted to RNA for example by subcloning the DNA into a transcriptional vector, such as pGEM family of plasmid vectors, or under control of a transcriptional. promoter of a virus such as vaccinia, and the RNA used as a naked RNA vaccine. The naked DNA or RNA vaccine can be injected alone, or combined with one or more DNA or RNA vaccines directed to the virus.

The naked DNA or RNA vaccine of the present invention can be administered for example intermuscularly, or alternatively, can be used in nose drops. The DNA or RNA fragment or a portion thereof can be injected as naked DNA or RNA, as DNA or RNA encapsulated in liposomes, as DNA or RNA entrapped in proteoliposomes containing viral envelope receptor proteins (Nicolau, C. et al. Proc. Natl. Acad. Sci. U.S.A. 1983, 80, 1068; Kanoda, Y., et al. Science 1989, 243, 375; Mannino, R. J. et al. Biotechniques 1988, 6, 682). Alternatively, the DNA can be injected along with a carrier. A carrier can be a protein or such as a cytokine, for example interleukin 2, or a polylysine-glycoprotein carrier (Wu, G. Y. and Wu, C. H. J. Biol. Chem. 1988, 263, 14621), or a non-replicating vector, for example expression vectors containing either the Rous sarcoma virus or cytomegalovirus promoters. Such carrier proteins and vectors and methods for using same are known to a person in the art (See for example, Acsadi, G. et al. Nature 1991, 352, 815-818). In addition, the DNA or RNA could be coated onto tiny gold beads and the beads introduced into the skin with, for example, a gene gun (Cohen, J. Science 1993, 259, 1691-1692; Ulmer, J. B. et al. Science 1993, 259, 1745-1749).

The invention also provides methods for treating a viral infection, e.g., HIV infection, in an animal by gene therapy. A variety of gene therapy approaches may be used to introduce nucleic acid encoding a fragment of the Tsg101 protein in vivo into cells so as to produce Tsg101 antibodies.

Any of the methods for gene therapy available in the art can be used according to the present invention. Exemplary methods are described below. For general reviews of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIBTECH 11(5):155-215). Methods commonly known in the art of recombinant DNA technology which can be used are described in Ausubel et al. (eds.), 1993, Current Protocols in Molecular Biology, John Wiley & Sons, New York; and Kriegler, 1990, Gene Transfer and Expression, A Laboratory Manual, Stockton Press, New York.

In a preferred aspect, the therapeutic comprises a Tsg101 nucleic acid that is part of an expression vector that expresses a Tsg101 or fragment or chimeric protein thereof in a suitable host. In particular, such a nucleic acid has a promoter operably linked to the Tsg101 coding region, said promoter being inducible or constitutive, and, optionally, tissue-specific. In another particular embodiment, a nucleic acid molecule is used in which the Tsg101 coding sequences and any other desired sequences are flanked by regions that promote homologous recombination at a desired site in the genome, thus providing for intrachromosomal expression of the Tsg101 nucleic acid (see e.g., Koller and Smithies, 1989, Proc. Natl. Acad. Sci. U.S.A. 86:8932-8935; Zijlstra et al., 1989, Nature 342:435-438).

Delivery of the nucleic acid into a patient may be either direct, in which case the patient is directly exposed to the nucleic acid or nucleic acid-carrying vector, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the nucleus, by administering it in linkage to a ligand subject to receptor-mediated endocytosis (see e.g., Wu and Wu, 1987, J. Biol. Chem. 262:4429-4432) (which can be used to target cell types specifically expressing the receptors), etc. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. U.S.A. 86:8932-8935; Zijlstra et al., 1989, Nature 342:435-438).

In a specific embodiment, a viral vector that contains the Tsg101 nucleic acid is used. For example, a retroviral vector can be used (see Miller et al., 1993, Meth. Enzymol. 217:581-599). These retroviral vectors have been modified to delete retroviral sequences that are not necessary for packaging of the viral genome and integration into host cell DNA. The Tsg101 nucleic acid to be used in gene therapy is cloned into the vector, which facilitates delivery of the gene into a patient. More detail about retroviral vectors can be found in Boesen et al., 1994, Biotherapy 6:291-302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, J. Clin. Invest. 93:644-651; Kiem et al., 1994, Blood 83:1467-1473; Salmons and Gunzberg, 1993, Human Gene Therapy 4:129-141; and Grossman and Wilson, 1993, Curr. Opin. Genet. and Devel. 3:110-114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson (1993, Current Opinion in Genetics and Development 3:499-503) present a review of adenovirus-based gene therapy. Bout et al. (1994, Human Gene Therapy 5:3-10) demonstrated the use of adenovirus vectors to transfer genes to the respiratory epithelia of rhesus monkeys. Other instances of the use of adenoviruses in gene therapy can be found in Rosenfeld et al., 1991, Science 252:431-434; Rosenfeld et al., 1992, Cell 68:143-155; and Mastrangeli et al., 1993, J. Clin. Invest. 91:225-234.

Adeno-associated virus (AAV) has also been proposed for use in gene therapy (Walsh et al., 1993, Proc. Soc. Exp. Biol. Med. 204:289-300).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, 1993, Meth. Enzymol. 217:599-618; Cohen et al., 1993, Meth. Enzymol. 217:618-644; Cline, 1985, Pharmac. Ther. 29:69-92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. In a preferred embodiment, epithelial cells are injected, e.g., subcutaneously. In another embodiment, recombinant skin cells may be applied as a skin graft onto the patient. Recombinant blood cells (e.g., hematopoietic stem or progenitor cells) are preferably administered intravenously. The amount of cells envisioned for use depends on the desired effect, patient state, etc., and can be determined by one skilled person in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, a Tsg101 nucleic acid is introduced into the cells such that it is expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention. Such stem cells include but are not limited to hematopoietic stem cells (HSC), stem cells of epithelial tissues such as the skin and the lining of the gut, embryonic heart muscle cells, liver stem cells (PCT Publication WO 94/08598), and neural stem cells (Stemple and Anderson, 1992, Cell 71:973-985).

Epithelial stem cells (ESCs) or keratinocytes can be obtained from tissues such as the skin and the lining of the gut by known procedures (Rheinwald, 1980, Meth. Cell Bio. 21A:229). In stratified epithelial tissue such as the skin, renewal occurs by mitosis of stem cells within the germinal layer, the layer closest to the basal lamina. Stem cells within the lining of the gut provide for a rapid renewal rate of this tissue. ESCs or keratinocytes obtained from the skin or lining of the gut of a patient or donor can be grown in tissue culture (Rheinwald, 1980, Meth. Cell Bio. 21A:229; Pittelkow and Scott, 1986, Mayo Clinic Proc. 61:771). If the ESCs are provided by a donor, a method for suppression of host versus graft reactivity (e.g., irradiation, drug or antibody administration to promote moderate immunosuppression) can also be used.

With respect to hematopoietic stem cells (HSC), any technique which provides for the isolation, propagation, and maintenance in vitro of HSC can be used in this embodiment of the invention. Techniques by which this may be accomplished include (a) the isolation and establishment of HSC cultures from bone marrow cells isolated from the future host, or a donor, or (b) the use of previously established long-term HSC cultures, which may be allogeneic or xenogeneic. Non-autologous HSC are used preferably in conjunction with a method of suppressing transplantation immune reactions of the future host/patient. In a particular embodiment of the present invention, human bone marrow cells can be obtained from the posterior iliac crest by needle aspiration (see e.g., Kodo et al., 1984, J. Clin. Invest. 73:1377-1384). In a preferred embodiment of the present invention, the HSCs can be made highly enriched or in substantially pure form. This enrichment can be accomplished before, during, or after long-term culturing, and can be done by any techniques known in the art. Long-term cultures of bone marrow cells can be established and maintained by using, for example, modified Dexter cell culture techniques (Dexter et al., 1977, J. Cell Physiol. 91:335) or Witlock-Witte culture techniques (Witlock and Witte, 1982, Proc. Natl. Acad. Sci. U.S.A. 79:3608-3612).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Additional methods that can be adapted for use to deliver a nucleic acid encoding a Tsg101 fragment of the invention or functional derivative thereof are described below.

5.5. Kits

The invention also provides kits containing the anti-TSG101 antibodies of the invention, or one or more TSG101 polypeptides which can be used to raise anti-TSG101 antibodies, or one or more nucleic acids encoding polypeptide anti-TSG101 antibodies of the invention, or cells transformed with such nucleic acids, in one or more containers. The nucleic acids can be integrated into the chromosome, or exist as vectors (e.g., plasmids, particularly plasmid expression vectors). Kits containing the pharmaceutical compositions of the invention are also provided.

6. EXAMPLES

The following examples are presented by way of illustration of the present invention, and are not intended to limit the present invention in any way.

6.1. Example 1

Preparation and Uses of Anti-TSG101 Antibodies

To determine the effect of anti-TSG101 antibodies on viral infections, a retroviral infection assay was developed. A murine leukemia virus (MLV) derived vector which contains an *E. coli* lacZ gene expressed from the long terminal repeat (LTR) promoter (pBMN-Z-I-Neo) was transfected into an amphotropic murine leukemia retroviral packaging cell line derived from 293 cells (Phoenix A, ATCC). Retroviruses produced by the Phoenix A helper cells were collected and used to infect a mouse N2A cells (ATCC). Anti-TSG101 antibodies were added to 293 helper cells 24 hours after the transfection of the MLV vector. The effectiveness of TSG101 antibodies on viral production was determined by the efficiency of viral supernatant to infect the target cells (N2A). The infection of N2A cells was then determined by cellular staining of β-galactosidase activity (positive cells were stained blue, showed as dark spots in FIG. 2).

Typically, phoenix A cells were seeded on poly-D-lysine coated 6-well plate a day before transfection. Four microgram of pBMN-Z-I-Neo was then transfected into each well in the presence of 12 ul of Lipofectamine 2000 (Invitrogen). Twenty-four hours post-transfection, media were replaced with 1 ml/well of fresh media containing trichostatin A (3 uM) and 5 or 10 ug of proper anti-TSG101 antibodies. 24 to 48 hours later, viral supernatants were collected, filtered with 0.2 um filters, and 1 ml of viral supernatant was mixed with 1 ml of fresh media containing polybrene (10 ug/ml), and then used to infect one well of N2a cells. 48 hours post-infection, N2a cells were fixed and stained with X-Gal as described in the β-Gal staining kit (Invitrogen). Results were documented by digital images.

In the following experiments, two anti-TSG101 antibodies were tested for their effect on viral infection, a rabbit antibody against N-terminal TSG101 protein, and a rabbit antibody against C-terminal TSG101 protein. The anti-N terminal TSG101 antibody was raised using a N-terminal fragment of the human TSG101 protein: VRETVNVITLYKDLKPVL (SEQ ID NO:2). The anti-C terminal TSG101 antibody was raised using a C-terminal fragment of the human TSG101 protein: QLRALMQKARKTAGLSDLY (SEQ ID NO:3). Rabbit IgG was used as non-specific antibody control. More than 10 independent experiments were performed, and representative results are shown in FIG. 2. Phoenix helper cells without treatment of antibody (positive control) showed efficient production of retroviruses, and infection of N2A target cells (left top panel); Rabbit IgG had no effect (left middle panel). The rabbit antibody against N-terminal TSG101 showed about 20%-60% inhibition (left bottom panel). But the rabbit antibody against C-terminal TSG101 significantly inhibited the production of retroviruses, and infection of N2A target cells (50-70% inhibition, right top panel). A mixture of the anti-C terminal and anti-N terminal antibodies gave similar results as the anti-C terminal antibody alone (Right middle panel). N2a cells that were not infected by viruses only showed minimal background staining (right bottom panel).

Similar results were also obtained in HIV viral infection assays.

6.2. Example 2

TSG101 Localized on Cell Surface During Viral Budding

This example shows that domains of TSG101 are exposed on cell surface during HIV release, and anti-TSG101 antibodies inhibited HIV release and infection.

1. TSG101 Localization During Viral Release

To demonstrate TSG101 is actively involved viral release at plasma membrane, an expression vector of GFP-TSG101 fusion protein was constructed and transfected into Phoenix cells (a retroviral helper cell line developed by Nolan et al of Stanford university) that was actively producing M-MuLV viruses. 24 hours after transfection, GFP-TSG101 fusion protein traffic was observed under confocal microscope (Ultraview, Perkin-Elmer). FIGS. 3A-E show a time course of images of GFP-TSG101 protein translocation from cytoplasm onto cell surface, and then "budding" out of the viral producing cells.

2. Cell Surface Localization of TSG101 During HIV Budding

Figure 4:
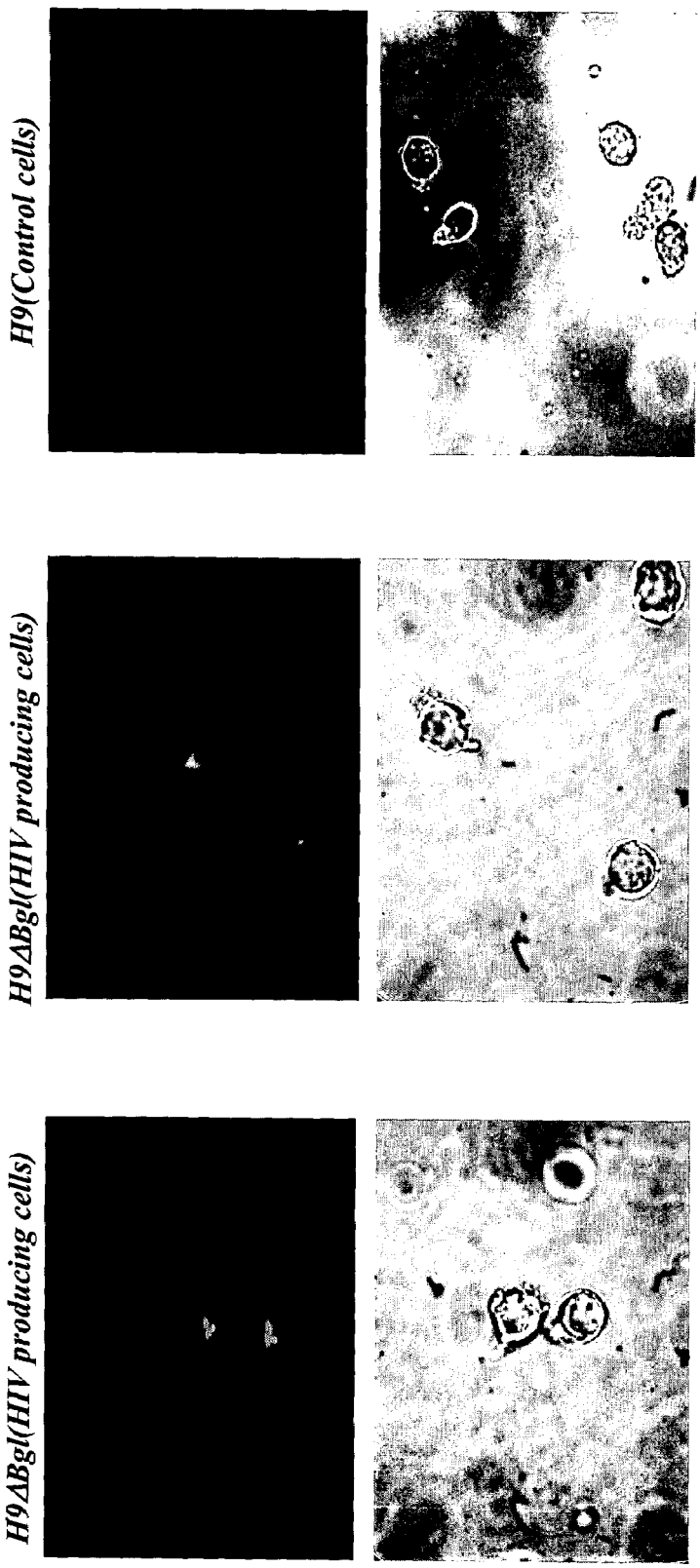

To determine if TSG101 is also actively involved in HIV budding, anti-TSG101 antibodies were used to directly detect cell surface TSG101 in a human CD4+ human T cell line H9 transfected with HIV (designated as H9ΔBgl), and the untransfected H9 cells were used as control. The two rabbit anti-TSG101 polyclonal antibodies, one against N-terminal (designated as anti-TSG101 "C") and one against C-terminal TSG101 (designated as anti-TSG101 "E"), were used for this study. Both antibodies have been well characterized (Li et al., 2001, Proc Natl Acad Sci USA 98(4): 1619-24). Both antibodies specifically detected cell surface localization of TSG101 only in HIV producing H9ΔBgl cells, and no cell surface TSG101 was detected in control H9 cells(FIG. 4). Interestingly, anti-TSG101 antibodies detected a "capping" like budding structure as observed with anti-HIV antibodies (Lee et al.,1999, J Virol. 73:5654-62).

3. FACS Profile of Cell Surface Localization of TSG101 During HIV Budding

Figure 5:
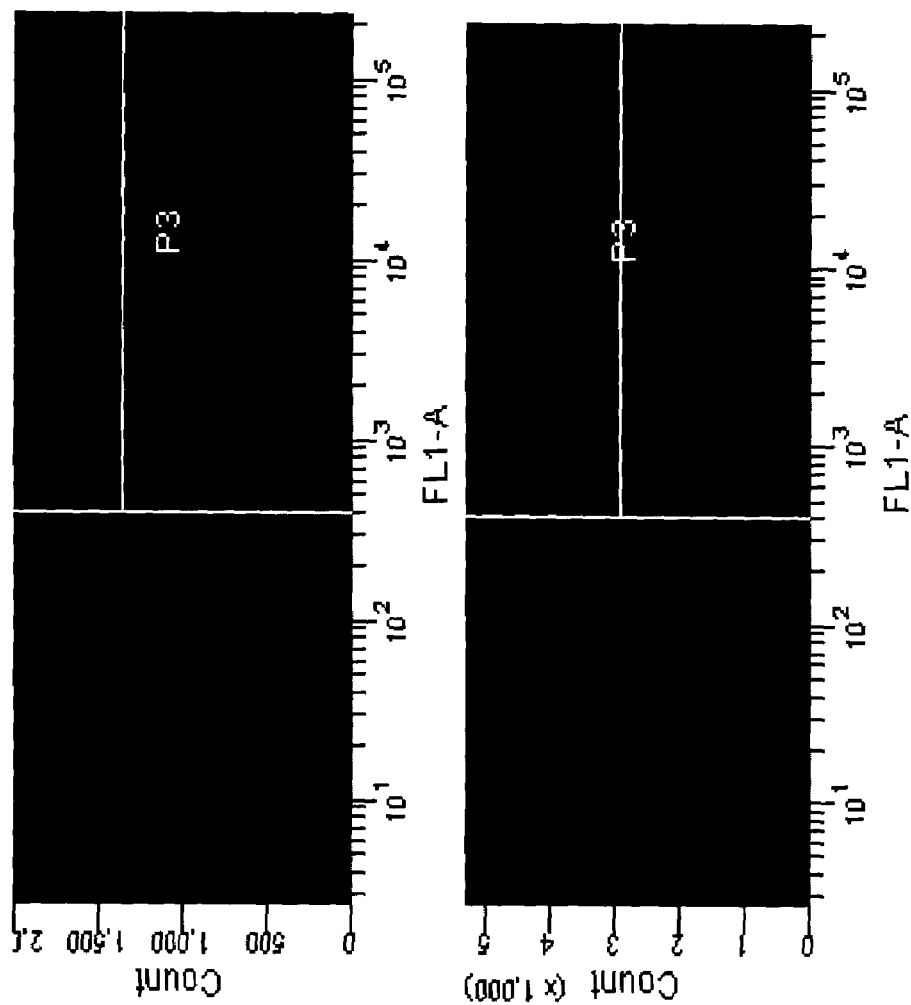

Cell surface localization of TSG101 in HIV producing cells (H9ΔBgl) and control H9 cells was then examined by Fluorescence Activated Cell Sorter (FACS). Both H9ΔBgl and H9 cells were fixed, stained with anti-TSG101 antibodies, and detected with a fluorescence labeled secondary antibody. The immuno-stained cells were analyzed on FACS. More than six independent experiments showed that about 70-85% H9ΔBgl cells were stained positive for surface TSG101, while less than about 0.1% H9 control cells were stained positive for surface TSG101 (FIG. 5). These results were further confirmed by direct examination of both H9ΔBgl and H9 control cells under confocal microscope. The small population (less than 0.1%) of H9 control cells resulted from weak background fluorescence signals associated with immunostaining procedure after confocal microscope analysis. The positive population of H9ΔBgl cells showed bright fluorescence.

4. Anti-TSG101 Antibody Inhibition of HIV Production in Transfected 293 Cells

Figure 6:
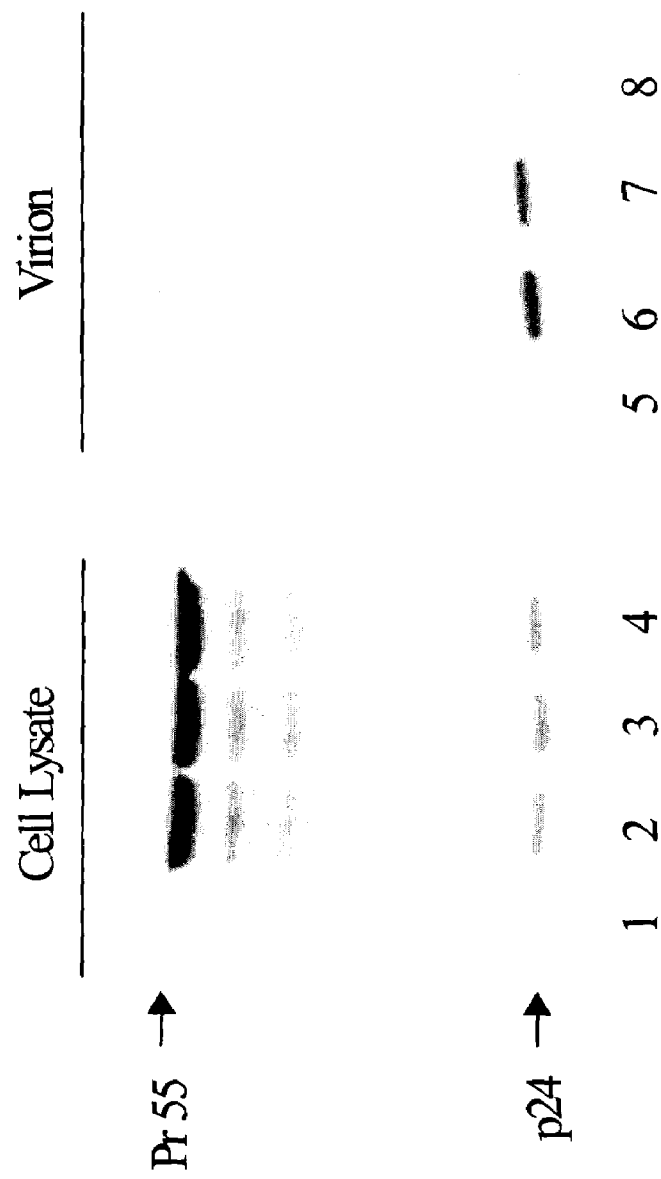

A HIV-1 viral production assay was used to further examine the inhibitory effect of TSG101 on retroviral production. The HIV-1 vector pNL4-3 was transfected into 293T cells. 24 hours after transfaction, two anti-TSG101 antibodies (10 ug/ml), anti-TSG101 antibody "E" and anti-TSG101 antibody "B", and a non-specific control antibody (10 ug/ml) were added respectively into the cell cultures. Anti-TSG101 antibody "B" was raise against a murine TSG101 N-terminal fragment and binds poorly to human TSG101 protein. Anti-TSG101 antibody "B" was used as a control. After an additional 24 hours incubation, cell lysates were extracted, cell culture supernatants were collected and HIV-1 virions were purified by sucrose gradients. Both cell lysates and purified virions were analyzed by Western blot using two anti-HIV-1 antibodies (anti-p55 and anti-p24). As shown in FIG. 6, anti-TSG101 antibody "E" treatment showed significant inhibition of HIV-1 virion release (more than 70% inhibition by density tracing of the Western blots, Lane 8), while anti-TSG101 antibody "B" (Lane 7) and the control antibody (Lane 6) did not show significant inhibition of HIV-1 release.

5. Antibody Inhibition of HIV Release from Human CD4+ T Lymphocytes (H9ΔBgl Cells)

Figure 7:
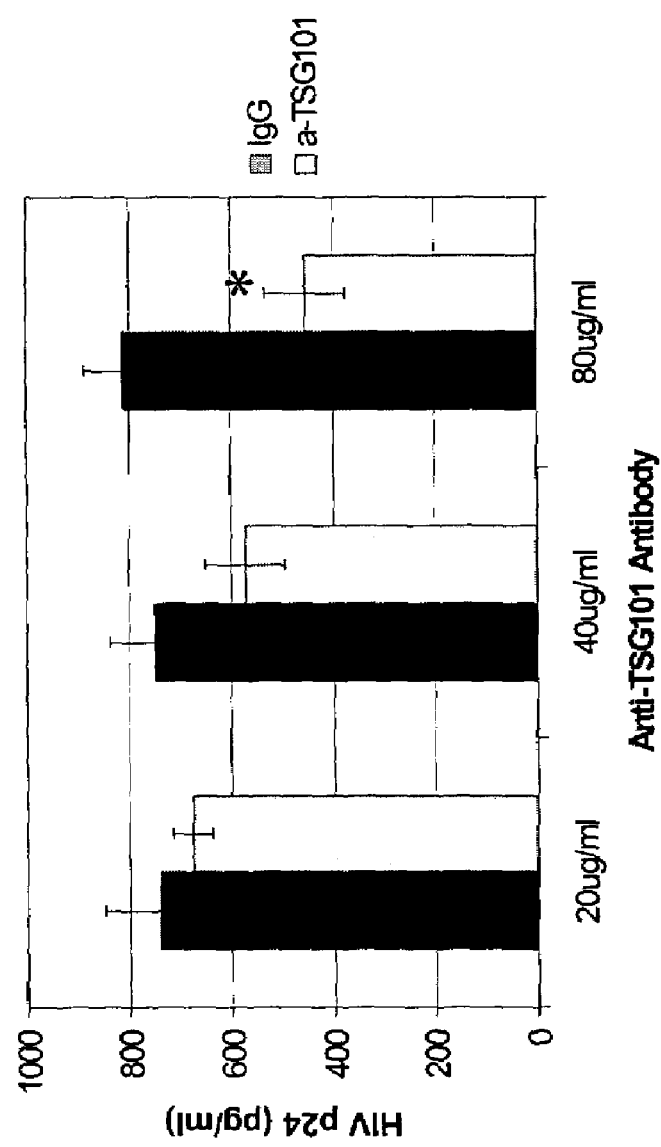

To specifically examine the effect of an antibody on HIV release, a HIV release assay based on H9ΔBgl cells was developed. H9ΔBgl cells are human CD4+ T lymphocytes transfected with an envelop-defective HIV construct (deletion of a Bgl II fragment of HIV genome). The stably transfected H9ΔBgl cells produce a non-infectious form of HIV (due to the defective HIV envelop, hence cannot infect other H9ΔBgl cells in the culture), HIV release from H9ΔBgl cells can be directly measured by HIV p24 ELISA of cell culture supernatant. Several concentrations of TSG101 antibody "E" and control antibody (rabbit IgG at the same concentrations) were used to incubate with H9ΔBgl cells. 48 hours after antibody addition, culture supernatants were collected for HIV p24 ELISA. Significant antibody inhibition of viral release was observed at 80 ug/ml (FIG. 7).

6. Antibody Inhibition of HIV Infectivity

Figure 8:
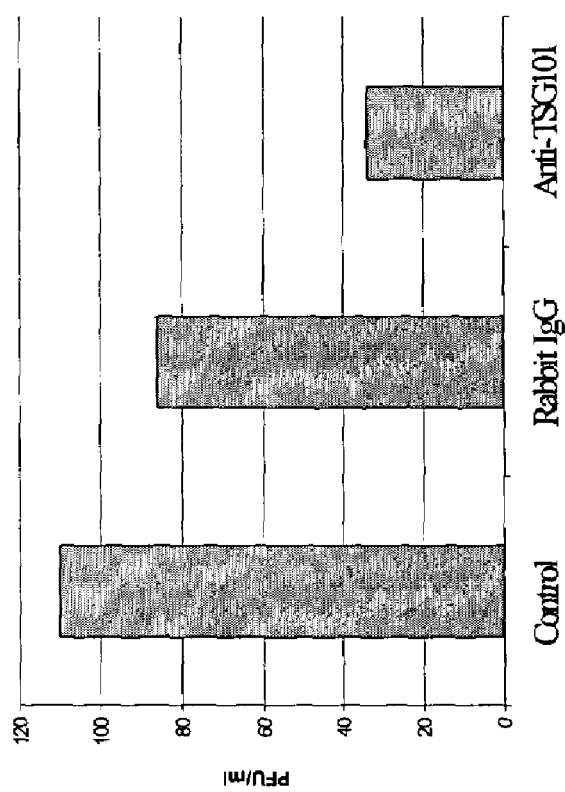

To determine if anti-TSG101 antibody has additional effect on HIV infectivity following viral release, HIV supernatants from Jurkat cells were used to infect MAGI cells in the presence of anti-TSG101 antibody "E" and rabbit IgG as controls (40 ug/ml). Anti-TSG101 antibody showed significant inhibition of HIV infectivity (FIG. 8), suggesting TSG101 has a role in HIV maturation and/or infection of target cells following viral release.

6.3. Example 3

Anti-TSG101 Antibodies Inhibit Release of Ebola Virus

This Example shows that TSG101 interacts with EBOV VP40, that TSG101 is incorporated into EBOV VLPs, and that anti-TSG101 antibody inhibits the release of EBOV virus-like particles (VLPs).

The only members of the family Filoviridae, EBOV and MARV possess a negative-stranded, non-segmented 19 Kb RNA genome comprising 7 genes: nucleoprotein(NP), viral proteins VP35, VP40, glycoprotein (GP), VP30, VP24, and RNA polymerase(L), encoding for seven proteins in MARV and eight proteins in EBOV. Recent studies provide some insights in the cellular localization and role of VP40, a 326 amino acid matrix (M) protein (Jasenosky et al., 2001, J Virol 75(11): 5205-14; Kolesnikova et al., 2002, J Virol 76(4): 1825-38). In cells infected with either EBOV or MARV, the majority of VP40 is peripherally associated with the cytoplasmic face of the plasma membrane via hydrophobic interactions. Significantly, expression of EBOV and MARV VP40 in transfected cells is required for the production of virus-like particles (VLPs), non-infectious particles that have some morphological properties similar to authentic viruses. The ability of VP40 to direct its own release from infected cells was mapped to a proline-rich sequence motif common to other enveloped RNA viruses (Harty et al., 2000, Proc Natl Acad Sci USA 97(25): 13871-6).

Figure 9:
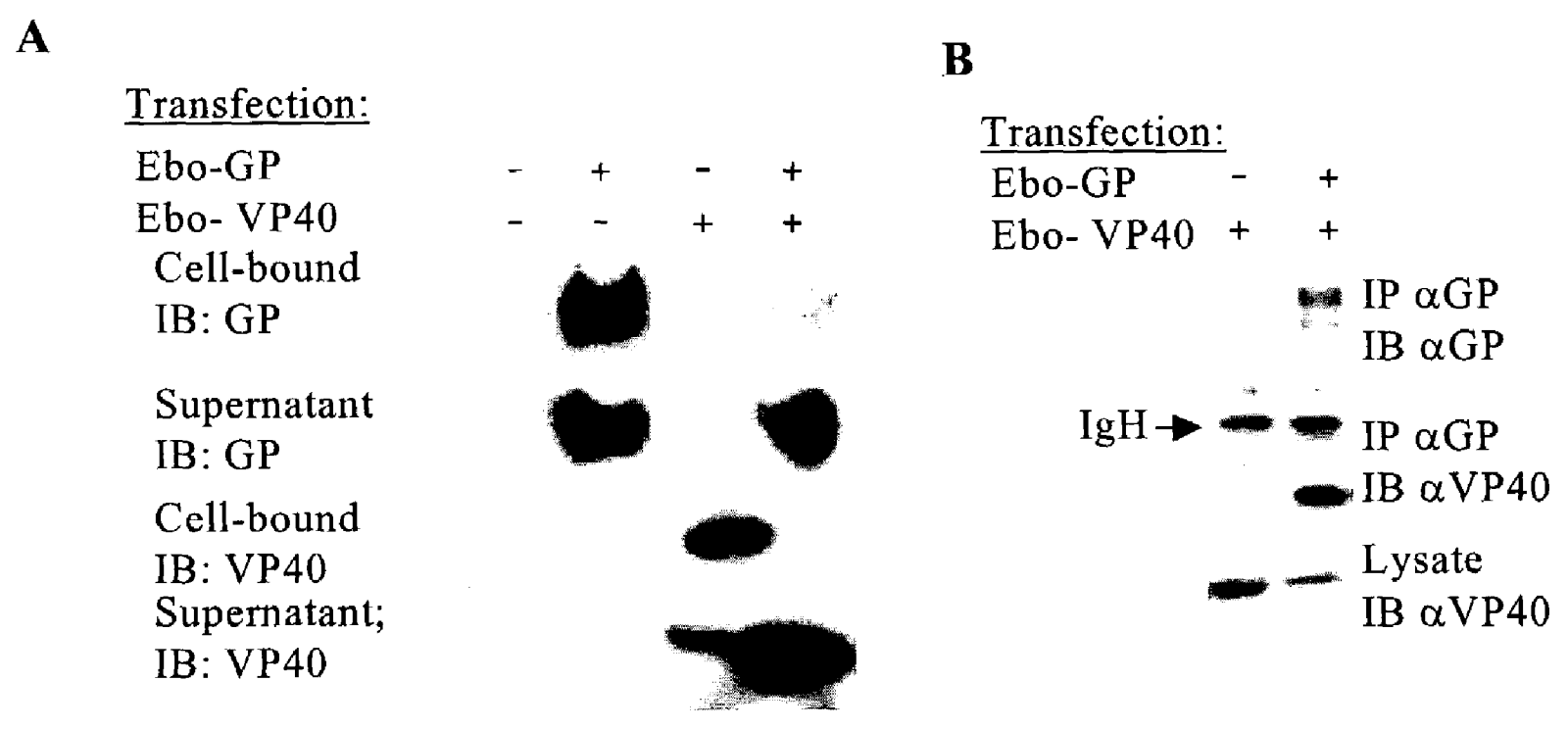

1. Generation of Virus-Like Particles as a Surrogate Model for Ebola Assembly and Release Several virus-like particles can be generated by mere expression of viral matrix proteins (Johnson et al., 2000, Curr Opin Struct Biol 10, 229-235). EBOV and MARV matrix proteins (VP40) have been shown to localize to both the plasma membrane and viral inclusion bodies (Kolesnikova et al., 2002, J Virol 76(4): 1825-38; Martin-Serrano et. al., 2001, Nature Medicine 7:1313-19), suggesting that VP40 may drive the assembly and release of mature virions. However, attempts to efficiently generate VLPs by expression of VP40 alone have been largely unfruitful, marked by inefficient release of amorphous VP40-containing material (Bavari et al., 2002, J Exp Med 195, 593-602). In retroviruses, the raft localization of the assembly complex is regulated by the association of N-terminally acylated Gag proteins (Campbell, et al., 2001, J Clin Virol 22, 217-227), whereas raft targeting of filovirus proteins such as VP40 appear to be mainly regulated by the viral glycoprotein (GP) (Bavari et al., 2002, J Exp Med 195, 593-602). Therefore, it was hypothesized that generation of filovirus VLPs may require coexpression of both GP and VP40. Whether GP and VP40 are released into culture supernatants was first examined. In cells expressing either GP or VP40 alone both proteins could be detected both in cells and supernatants (FIG. 9A). Coexpression of both proteins, however, resulted in substantial increase in release from cells (FIG. 9A). It was reasoned that if the released GP and VP40 are associated in particles, VP40 must be co-immunoprecipitated with anti-GP mAb. As shown in FIG. 9B, VP40 was readily detected in anti GP-immunoprecipitates from the supernatants of cells transfected with both GP and VP40 of EBOV. No VP40 was pulled down from the supernatant of cells expressing VP40 alone, showing that the co-IP is specific.

Figure 10:
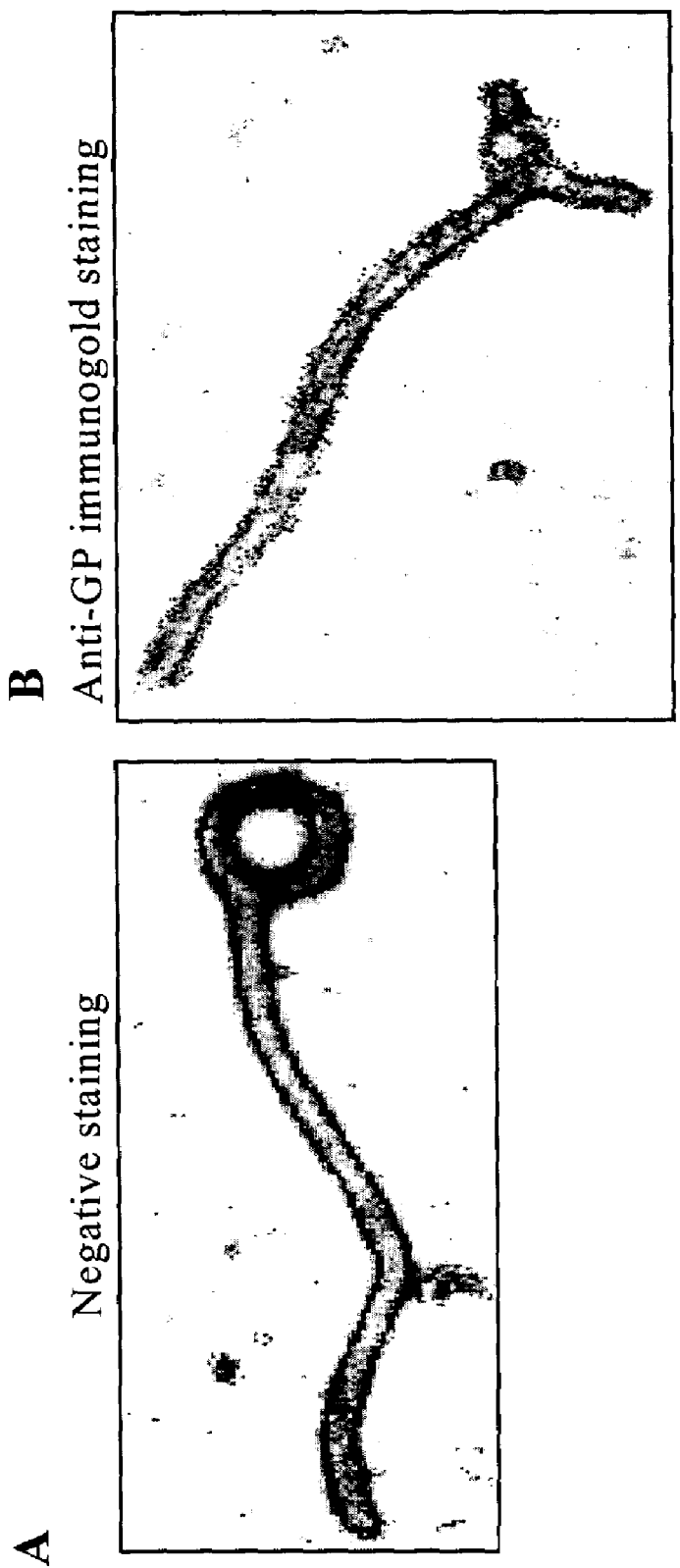

2. Particles Formed by EBOV GP and VP40 Display the Morphological Characteristics of Ebola Virus The co-IP experiments demonstrated that GP and VP40 released into supernatant are associated with each other in some form. To determine whether these complexes represent virus-like particles (VLPs), particulate material from culture supernatants was purified by sucrose gradient ultracentrifugation (Bavari et al., 2002, J Exp Med 195, 593-602) and analyzed using electron microscopy. Interestingly, most of the particles obtained from the supernatants of the cells cotransfected with GP and VP40 displayed a filamentous morphology strikingly similar to filoviruses (FIGS. 10A and B) (Geisbert, et al.,1995, Virus Res 39, 129-150; Murphy et al.,1978, Ebola and Marburg virus morphology and taxonomy, 1 edn (Amsterdam, Elsvier)). In contrast, the material obtained from singly transfected cells only contained small quantities of membrane fragments, likely released during cell death. The VLPs have a diameter of 50-70 nm and are 1-2 μm in length (FIG. 10). This is similar to the length range of Ebola virions found in cell culture supernatants after in vitro infection (Geisbert, et al.,1995, Virus Res 39, 129-150). The smaller diameter of VLPs (as compared to 80 nm for EBOV) may be due to the lack of ribonucleoprotein complex. All types of morphologies described for filoviruses such as branched, rod-, U- and 6-shaped forms (Feldmann et al.,1996, Adv Virus Res 47, 1-52; Geisbert, et al.,1995, Virus Res 39, 129-150) among these particles were observed (FIG. 10). In addition, the VLPs were coated with 5-10 nm surface projections or "spikes" (FIG. 10), characteristic for EBOV (Feldmann et al.,1996, Adv Virus Res 47, 1-52; Geisbert, et al., 1995, Virus Res 39, 129-150). Immunogold staining of the VLPs with anti-Ebola GP antibodies demonstrated the identity of the spikes on the surface of the particles as Ebola glycoprotein (FIG. 10B). VLPs for Marburg virus were also generated in a similar manner.

In summary, a surrogate assay for the assembly and release of Ebola virus that can be performed without the restrictions of biocontainment laboratories was established. This assay can be used for initial screenings of agents that may inhibit Ebola virus budding.

3. Studies on the Role of TSG101 in Ebola Virus Life Cycle

Figure 11:
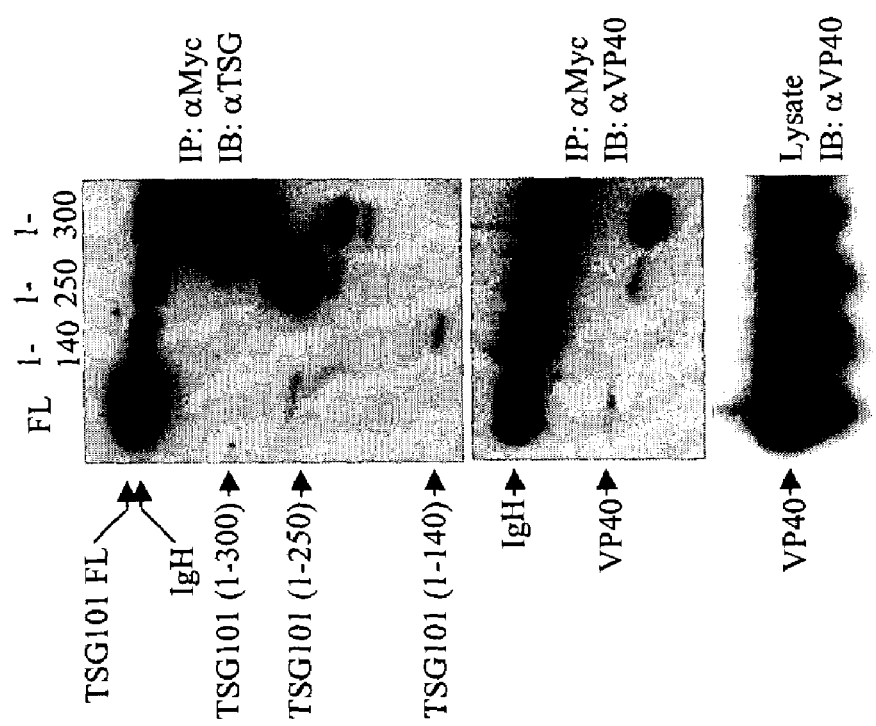

We performed a series of biochemical studies to examine the involvement of the vaccuolar protein sorting (vps) protein TSG101 interaction with the late domain of VP40 in EBOV assembly and release. A set of TSG101 truncations C-terminally tagged with a Myc epitope were used for these studies. 293T cells were transfected with full length TSG101 and mutants truncated at positions 140, 250 and 300 along with EBOV VP40. Cells were lysed after 48 h and subjected to immunoprecipitation with an anti-Myc antibody. As shown in FIG. 11, VP40 was coprecipitated with all TSG101 proteins except for the 1-140 truncated mutant. Lack of association with this mutant is consistent with the structural data that show that residues 141-145 make important contacts with an HIV Gag-derived PTAP peptide (Pornillos et al., 2002, Nat Struct Biol 9, 812-7). Interestingly, the association of VP40 with 1-300 mutant of TSG101 was significantly stronger than with full length or 1-250 mutant (FIG. 11). The lower association of full length TSG101 can be attributed to the presence of a PTAP motif in the C-terminal region of this molecule that may form an inter- or intramolecular association with the UEV domain of TSG101. The dramatic reduction of interaction resulting from deletion of amino acids 250-300 suggests that residues in this region may contribute to the binding to viral matrix proteins.

Figure 12:
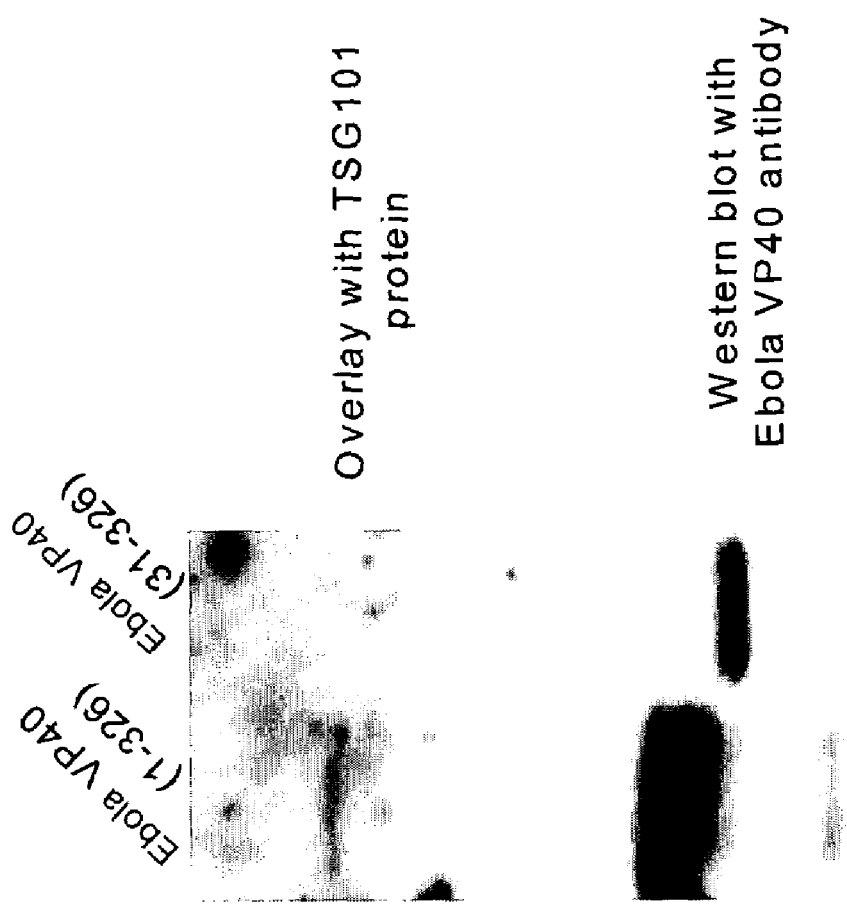
FIG. 12 shows Far-Western analysis of association between Ebola VP40 and TSG101 UEV domain.

To confirm that TSG101 and VP40 associate directly and through the PTAP motif, Far Western analysis was performed. Ebola VP40 (1-326) and truncated (31-326) Ebola VP40 proteins as well as HA-tagged UEV domain of TSG101 were produced in bacteria. These proteins were electrophoresed on 4-20% gradient gel and electroblotted onto nitrocellulose membrane. Following blocking, the blot was incubated with a purified TSG 101 protein (UEV), washed, and protein-protein interaction detected by enhanced chemiluminescence using an anti TSG101 antibody and HRP-labeled goat anti rabbit as secondary antibody. As shown in FIG. 12, TSG 101 interacts with the full length Ebola VP40 but not with the truncated Ebola VP40, confirming that the PTAP motif at the N terminus of VP40 plays a critical role in VP40-TSG101 (UEV) interaction. An identical western blot developed with Ebola VP40 antibody could detect both the full length and the truncated VP40 showing the presence of both the proteins on the blot.

Figure 13:
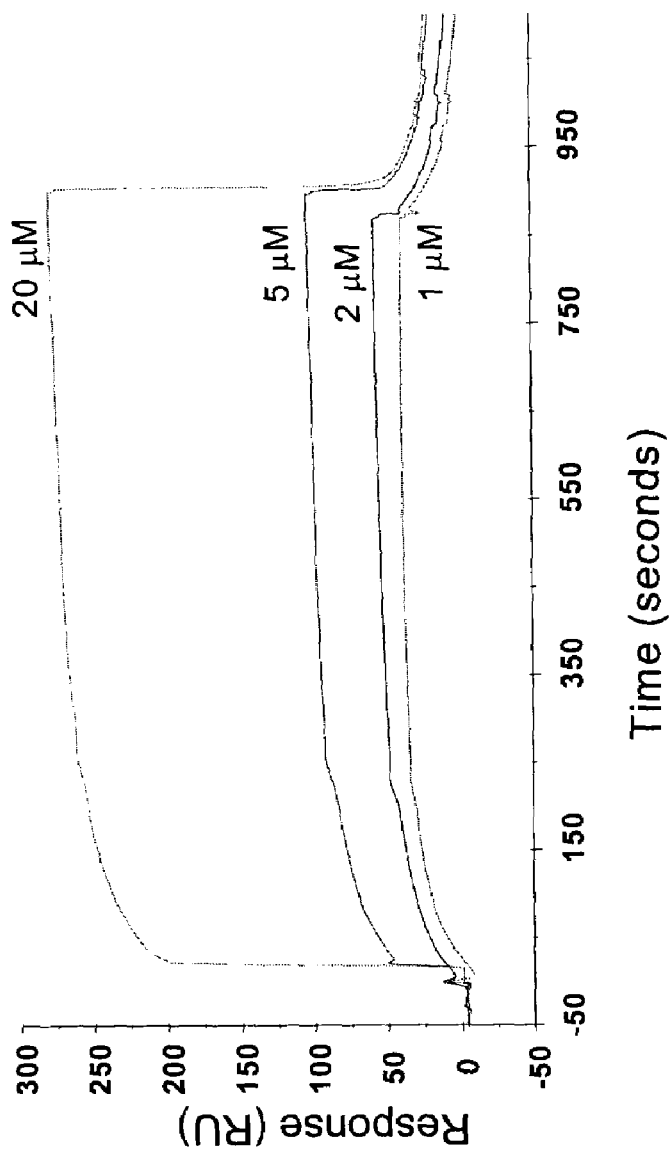
FIG. 13 shows SPR analysis of Ebola VP40 interaction with TSG101.

4. Surface Plasmon Resonance Biosensor (SPR) Analysis of the Ebola VP40-TSG101 Interaction A quantitative analysis of Ebola VP40 interacting with TSG101 was carried out using SPR measurements. A biotinylated peptide (Bio-ILPTAPPEYME) containing 11 amino acid residues from the N terminus of the Ebola VP40 was immobilized on the streptavidine chip. Purified TSG101 protein that contains only the UEV domain was injected at different concentrations (1, 2, 5, 20 uM) serially. As seen in the FIG. 13, an interaction of moderate affinity between the peptide and proteins can be detected. Based on the SPR data we calculated a KD value of ~2 µM for this interaction.

5. Incorporation of TSG101 in Ebola VLPs and Virions

To determine whether TSG101 is incorporated in EBOV VLPs, TSG101 (1-312) together with GP or GP+VP40 were expressed in 293T cells. VLPs were immunoprecipitated from supernatants using anti GP antibodies. Expression of TSG101(1-312) resulted in a marked increase in VLP release, suggesting a positive role for TSG101 in VLP budding (FIG. 14A, Lane 4). In addition, TSG101 (1-312) was coimmunoprecipitated with an anti-GP antibody from the culture supernatants when expressed along with GP and VP40 (FIG. 14A, Lane 4). No TSG101 was found associated with GP when expressed in the absence of VP40 (FIG. 14A, lane 3), suggesting that its association with GP was dependent on formation of VLPs. Similar results were also obtained with full length TSG101. These data strongly suggest that TSG101 is incorporated into VLPs and support the hypothesis that TSG101 plays a role in viral assembly and/or budding. To further substantiate this finding we also analyzed inactivated, band purified, EBOV (iEBOV) for the presence of TSG101. 5 µg iEBOV were analyzed by immunoblotting for the presence of TSG101. As shown in FIG. 6B, we found readily detectable levels of TSG101 in iEBOV, clearly demonstrating the incorporation of TSG101 in Ebola virus.

6. Effect of Polyclonal Anti TSG101 Antibodies on Ebola Virus Release

The biochemical and VLP release data suggested that TSG101 is critical for the egress of Ebola virus. Therefore, the effects of polyclonal anti-TSG 101 antibodies "C" and "E" (that showed inhibitory effect on HIV, see Examples 1 and 2) were tested on the virus production in Hela cells infected with Ebola Zaire-95 virus. Monolayers of Hela cells were incubated with the virus at an MOI of 1 for 50 minutes, washed, and a medium containing an anti-TSG101 antibody or a control rabbit anti mouse antibody were added at 5 µg/ml. After 24 hours the supernatants were harvested and the released viruses enumerated by plaque assay as previously described (Bavari et al., 2002, J Exp Med 195, 593-602). As shown in FIG. 15, these antibodies partially inhibited the release of virions into Hela cell supernatant.

7. References Cited

All references cited herein are incorporated herein by reference in their entirety and for all purposes to the same extent as if each individual publication or patent or patent application was specifically and individually indicated to be incorporated by reference in its entirety for all purposes.

Many modifications and variations of the present invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

What is claimed is:

1. A method for inhibiting virus budding by an enveloped virus in a mammal, comprising administering to said mammal a therapeutically effective amount of an antibody, wherein said antibody that binds a TSG 101 protein and wherein said antibody binds an epitope in a region selected from the group consisting of VRETVNVITLYKDLKPVL (SEQ ID NO:2) and QLRALMQKARKTAGLSDLY (SEQ ID NO:3), whereby viral budding by said enveloped virus is inhibited.

2. The method of claim 1, wherein said antibody binds the N-terminal or C-terminal region of said TSG101 protein.

3. The method of claim 2, wherein said mammal is a human.

4. The method of claim 1, wherein said enveloped virus is selected from the group consisting of human immunodeficiency virus type I (HIV-I), human immunodeficiency virus type II (HIV-II), Marburg virus, and Ebola virus.

5. The method of any one of claims 1-3 and 4, wherein said antibody is a monoclonal antibody.

6. The method of claim 1, further comprising administering to said mammal a therapeutically effective amount of one or more other therapeutic agents.

* * * * *